US012667677B2

(12) United States Patent
Denny et al.

(10) Patent No.: US 12,667,677 B2
(45) Date of Patent: Jun. 30, 2026

(54) CAPSULE INHALERS AND METHODS OF USING SAME

(71) Applicant: Knightpoint, LLC, Cary, NC (US)

(72) Inventors: John W Denny, Cary, NC (US); Jeffrey Warden, Bala Cynwyd, PA (US)

(73) Assignee: Knightpoint Group, LLC, Cary, NC (US)

( * ) Notice: Subject to any disclaimer, the term of this patent is extended or adjusted under 35 U.S.C. 154(b) by 467 days.

(21) Appl. No.: 18/361,220

(22) Filed: Jul. 28, 2023

(65) Prior Publication Data

US 2024/0042145 A1 Feb. 8, 2024

Related U.S. Application Data

(63) Continuation of application No. PCT/US2022/013976, filed on Jan. 27, 2022.

(Continued)

(51) Int. Cl.
*A61M 15/00* (2006.01)

(52) U.S. Cl.
CPC ........ *A61M 15/003* (2014.02); *A61M 15/002* (2014.02); *A61M 15/0025* (2014.02); *A61M 2202/064* (2013.01)

(58) Field of Classification Search
CPC .......... A61M 15/0005; A61M 15/0006; A61M 15/0008; A61M 15/002; A61M 15/0025;

(Continued)

(56) References Cited

U.S. PATENT DOCUMENTS

| | | | | |
|---|---|---|---|---|
| 4,206,758 A | * | 6/1980 | Hallworth ......... | A61M 15/0028 |
| | | | | 128/203.23 |
| 4,210,140 A | * | 7/1980 | James ............... | A61M 15/0028 |
| | | | | 604/59 |

(Continued)

FOREIGN PATENT DOCUMENTS

| | | | | |
|---|---|---|---|---|
| EP | 0581473 A1 | * | 2/1994 | ........ A61M 15/0043 |
| JP | H08103499 A | * | 4/1996 | ........ A61M 15/0028 |

(Continued)

*Primary Examiner* — Kathryn E Ditmer

(74) *Attorney, Agent, or Firm* — James G. Passe; Passe Intellectual Property, LLC

(57) ABSTRACT

The present disclosure describes a capsule inhaler. The capsule inhaler includes a main body including an inner cavity, a mouth section coupled to or integral with the main body and in fluid communication with the inner cavity, an actuator coupled to the main body, at least four longitudinally spaced apart nozzles residing within the main body positioned and configured to direct airflow into the inner cavity, and a cover coupled to the main body. The inner cavity is sized and configured to receive a capsule containing a dry powder formulation. One or more of the inner cavity, elongate member, and cover each are configured to engage with the capsule when inserted into the inner cavity and assist in separating the capsule to release the dry powder formulation into the inner cavity of the inhaler for inhalation by a subject. At least two of the nozzles are positioned and configured to direct airflow received from the at least one air intake port into separated segments of the capsule and at least another two of the nozzles are positioned and configured to direct bypass airflow received from the at least one air intake port into the inner cavity. Methods of using a capsule inhaler are also described herein.

28 Claims, 14 Drawing Sheets

Related U.S. Application Data

(60) Provisional application No. 63/149,811, filed on Feb. 16, 2021.

(58) Field of Classification Search
CPC ............ A61M 15/0028; A61M 15/003; A61M 15/0031; A61M 15/0043
See application file for complete search history.

(56) References Cited

U.S. PATENT DOCUMENTS

| | | | | |
|---|---|---|---|---|
| 4,446,862 A | * | 5/1984 | Baum ............... | A61M 15/0043 |
| | | | | 128/203.15 |
| 4,846,168 A | * | 7/1989 | Abiko ............... | A61M 15/0086 |
| | | | | 128/200.23 |
| 4,860,740 A | * | 8/1989 | Kirk .................. | A61M 15/0028 |
| | | | | 128/203.15 |
| 9,027,551 B2 | | 5/2015 | King et al. | |
| 2013/0152927 A1 | * | 6/2013 | Baillet .............. | A61M 15/0026 |
| | | | | 128/203.15 |
| 2015/0283338 A1 | * | 10/2015 | Colosio ............ | A61M 15/0028 |
| | | | | 128/203.15 |
| 2018/0036497 A1 | * | 2/2018 | Ventura ............. | A61M 15/0045 |
| 2018/0140789 A1 | | 5/2018 | Pieters et al. | |
| 2018/0264208 A1 | * | 9/2018 | Hemy ............... | A61M 15/0005 |

FOREIGN PATENT DOCUMENTS

| | | | | | |
|---|---|---|---|---|---|
| JP | 2006280676 A | * | 10/2006 | | |
| WO | WO-2015110832 A1 | * | 7/2015 | .......... | A61M 15/003 |
| WO | WO-2019215767 A9 | * | 12/2019 | ........ | A61M 15/0043 |

* cited by examiner

CAPSULE INHALERS AND METHODS OF USING SAME

RELATED APPLICATION(S)

The present application claims priority from and the benefit of PCT Application No. PCT/US2022/013976 filed on Jan. 27, 2022, which claims priority of U.S. Provisional Application Ser. No. 63/149,811, filed Feb. 16, 2021, the disclosure of which is hereby incorporated herein in its entirety.

FIELD OF THE INVENTION

The invention relates to medical devices, and more particularly, to capsule inhalers.

BACKGROUND

Inhalers are medical devices used for delivering medicines into the lungs through the work of a user's breathing, which provides the ability for targeted medical treatment to this specific region of the body. There are several known types of inhalers including meter-dosed inhalers, dry powder inhalers, soft mist inhalers, and nebulizers, each having their own advantages and disadvantages.

SUMMARY

Embodiments of the invention are directed to capsule inhalers sized and configured to receive a respective capsule containing dry powder agents/ingredients and to grip a first and/or second segment of the capsule without puncturing same to detach the first and second segments and release the dry powder agents/ingredients for inhalation delivery to a user.

Embodiments of the invention are directed to a capsule inhaler. The capsule inhaler may include a main body having an inner cavity, a backwall, and at least one air intake port. The inner cavity may be sized and configured to receive a capsule containing a dry powder formulation. The capsule inhaler may further include a mouth section coupled to or integral with the main body and in fluid communication with the inner cavity. The capsule inhaler may further include an actuator coupled to the main body. The actuator may include an elongate member attachable to an end portion of the capsule and may be configured to move between first and second positions to separate the capsule within the inner cavity. The capsule inhaler may further include at least four longitudinally spaced apart nozzles residing within the main body and in fluid communication with the inner cavity. Each nozzle extends between the inner cavity and backwall of the main body opposite the mouth section terminating adjacent to, but spaced apart from, the backwall leaving a gap between the nozzles and the backwall. The capsule inhaler may further include a cover coupled to the main body. One or more of the inner cavity, elongate member, and cover each may be configured to engage with a capsule when inserted into the inner cavity and assist in separating the capsule to release the dry powder formulation into the inner cavity of the inhaler for inhalation by a subject. At least two of the nozzles may be positioned and configured to direct airflow received from the at least one air intake port into separated segments of the capsule and at least another two of the nozzles may be positioned and configured to direct bypass airflow received from the at least one air intake port into the inner cavity.

According to some embodiments, the inhaler may include four nozzles.

According to some embodiments, the at least four longitudinally spaced apart nozzles may include a first pair of nozzles and second pair of nozzles. A first nozzle of the first pair of nozzles may be configured to direct airflow only into the first capsule segment and a first nozzle of the second pair of nozzles may be configured to direct airflow only into the second capsule segment. The second nozzle of the first pair of nozzles may direct airflow across the inner cavity over a first sub-length of the inner cavity and the second nozzle of the second pair of nozzles may be configured to direct airflow across the inner cavity over a second sub-length of the inner cavity whereby airflow from the second nozzles do not cross about the inner cavity.

According to some embodiments, airflow from each pair of nozzles may be directed such that it does not cross an imaginary center line extending laterally across the inner cavity and between the two pairs of nozzles.

According to some embodiments, two of the nozzles may have a narrower airpath passageway than the other two nozzles.

According to some embodiments, the airpath passageways of the nozzles may be tapered to narrow at an exit end of the nozzles.

According to some embodiments, at least two of the nozzles may create a partially rotational airflow within the separated segments of the capsule.

According to some embodiments, the elongate member of the actuator may include a spring-loaded assembly that bias the actuator against a capsule that has been inserted into the inner cavity.

According to some embodiments, the actuator may further include a head portion coupled to the elongate member providing a location for a user to grip the actuator.

According to some embodiments, the cover may include a visually transmissive segment allowing a user to see into the inner cavity of the inhaler when the cover is in a closed position.

According to some embodiments, the dry powder formulation within the capsule may include a pharmaceutical or nutraceutical.

According to some embodiments, the inner cavity may be sized to hold a size 0 capsule.

According to some embodiments, the inner cavity may have a length between about 0.85 inch and about 1.25 inches.

According to some embodiments, the actuator may be configured to separate the capsule within the inner cavity such that adjacent ends of the separated segments of the capsule are spaced apart a distance between about 0.60 inches and about 1 inch.

Further embodiments of the invention are directed to a capsule inhaler. The capsule inhaler may include a main body having an inner cavity formed therein. The inner cavity may be sized and configured to receive a capsule containing a dry powder formulation. The capsule inhaler may further include a mouth section coupled to or integral with the main body and in fluid communication with the inner cavity. The capsule inhaler may further include an actuator coupled to the main body, the actuator including an elongate member attachable to an end portion of the capsule. The actuator may be configured to move between first and second positions to separate the capsule within the inner cavity. The capsule inhaler may further include a first pair of nozzles and a second pair of nozzles, each pair of nozzles residing longitudinally spaced apart within the main body and in fluid communication with the inner cavity. The first and second pair of nozzles may extend between the inner cavity and a backwall of the main body and opposite the mouth section terminating adjacent to, but spaced part from, the backwall leaving a gap between the pairs of nozzles and the backwall. The capsule inhaler may further include a cover coupled to the main body. One or more of the inner cavity, elongate member, and cover each may be configured to engage with a capsule when inserted into the inner cavity and assist in separating the capsule to release the dry powder formulation into the inner cavity of the inhaler for inhalation by a subject. The first pair of the nozzles may be sized and configured to direct airflow into a first one of the capsule segments and the second pair of the nozzles may be sized and configured to direct bypass air into and/or across the inner cavity.

Further embodiments of the invention are directed to a method of delivering a dry powder agent to a subject. The method may include (a) providing a capsule inhaler including a main body having an inner cavity formed therein and at least one air intake port, a mouth section coupled to or integral with the main body, a mouth section coupled to or integral with the main body and in fluid communication with the inner cavity, an actuator coupled to the main body, the actuator including an elongate member attachable to an end portion of a capsule, the actuator being configured to move between first and second positions to separate the capsule within the inner cavity, at least four longitudinally spaced apart nozzles residing within the main body positioned and configured to direct airflow into the inner cavity; a cover coupled to the main body, and a cap removeable secured to the mouth section, the inner cavity, elongate member, and cover of the inhaler each are configured to engage an end portion of the capsule; (b) removing the cap from the mouth section; (c) opening the cover; (d) inserting a capsule having two releasably coupled cylindrical segments with opposing closed and open end portions and containing the dry powder agent into the inner cavity such that one segment of the capsule contacts the one or more gripping features of the inner cavity and the other segment contacts the one or more gripping features of the elongate member; (e) pivoting the cover to a closed position to secure one segment of the capsule between the one or more gripping features of the inner cavity and the one or more gripping features of the cover; (f) placing the subject's mouth over the mouth section of the inhaler; (g) pulling the actuator longitudinally outwardly from the main body of the inhaler to an opened position which simultaneously causes the elongate member to grip and pull one segment of the capsule as the other segment remains held in place between the one or more gripping features of the inner cavity and the cover, thereby separating the capsule and releasing the dry powder agent contained therein; and (h) inhaling by the subject to create an airflow stream from the at least one air intake port through the at least four nozzles into the inner cavity and separated capsule segments to receive the released the dry powder agent through the aperture of the mouth section.

According to some embodiments, the method may further include (i) pushing the actuator longitudinally inwardly toward the main body of the inhaler to a closed position; and (j) pivoting the cover to the opened position to remove the empty capsule.

According to some embodiments, the elongate member of the actuator may include a spring-loaded assembly that pushes the separated segments of the empty capsule out from the inner cavity.

According to some embodiments, the dry powder agent may include a pharmaceutical that is delivered to the subject to treat a disease.

According to some embodiments, the disease may be a respiratory disease selected from a group consisting of asthma, chronic obstructive pulmonary disease (COPD), lung cancer, and SARS-CoV-2 (COVID-19).

According to some embodiments, the dry powder agent may include a pharmaceutical that is delivered directly into the throat and/or esophagus of the subject to treat eosinophilic esophagitis (EoE).

According to some embodiments, the dry powder agent may include a pharmaceutical that is delivered to the subject to provide a hormone treatment via the stomach or lungs of the subject.

According to some embodiments, the dry powder agent may include a pharmaceutical that is delivered to the subject to treat an infection in the subject's lungs.

According to some embodiments, the dry powder agent may include a nutraceutical that is delivered to the subject to promote health.

According to some embodiments, the dry powder agent may be a dry powder pharmaceutical or dry powder nutraceutical.

According to some embodiments, the dry powder pharmaceutical or dry powder nutraceutical may be selected from a group consisting ciclesonide, Advair® or generics thereof, azithromycin, tiotropium, Symbicort® or generics thereof, remdesivir, oxytocin, levodopa, albuterol or other short acting beta agonists (SABA), salmeterol or other long acting beta agonists (LABA), fluticasone, budesonide, mometesone or other corticosteroids, Breo or generics thereof, Anoro or generics thereof, Trelegy or generics thereof, vilanterol, fluticasone furoate, umeclidinium bromide, tiotopium, ipratropium, long-acting muscarinic antagonists (*LAMA*), anti-infectives, antibiotics, tobramycin, antivirals, antifungals, mucalytics, cannabinoids, fentanyl, psilocybin, Vitamin D, and Zinc, and any combinations thereof.

According to some embodiments, the dry powder pharmaceutical or dry powder nutraceutical may be blended with one or more excipients, bulking agents and/or carriers.

According to some embodiments, the excipient, bulking agent, or carrier may be lactose, magnesium stearate, mannitol, or luceine.

According to some embodiments, the dry powder pharmaceutical may include vilanterol, fluticasone furoate, umeclidinium bromide, or a combination thereof.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim, accordingly, including the right to be able to amend any originally filed claim to depend from and/or incorporate any feature of any other claim although not originally claimed in that manner. These and other objects and/or aspects of the present invention are explained in detail in the specification set forth below.

5

Figure 1:
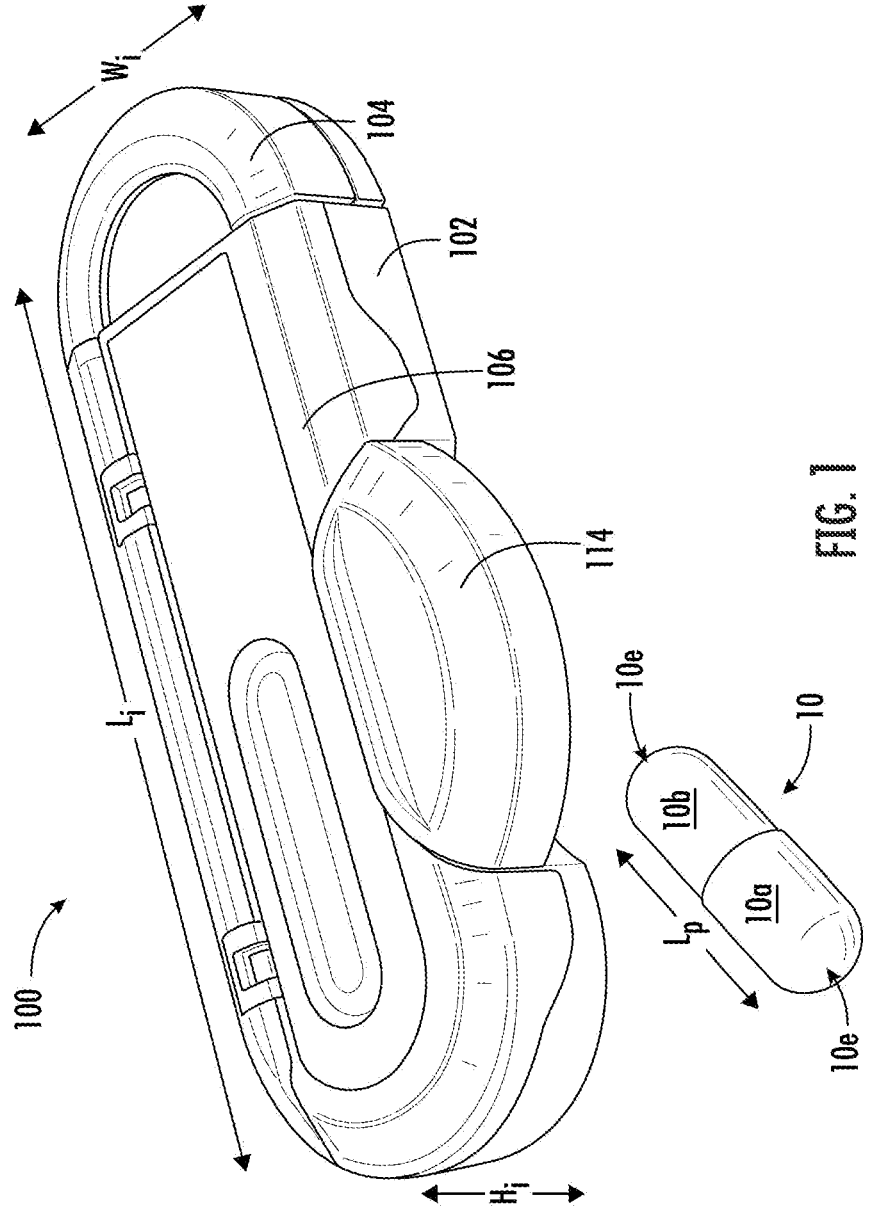
FIG. 1 is top perspective view of a capsule inhaler according to embodiments of the present invention.
Figure 2A:
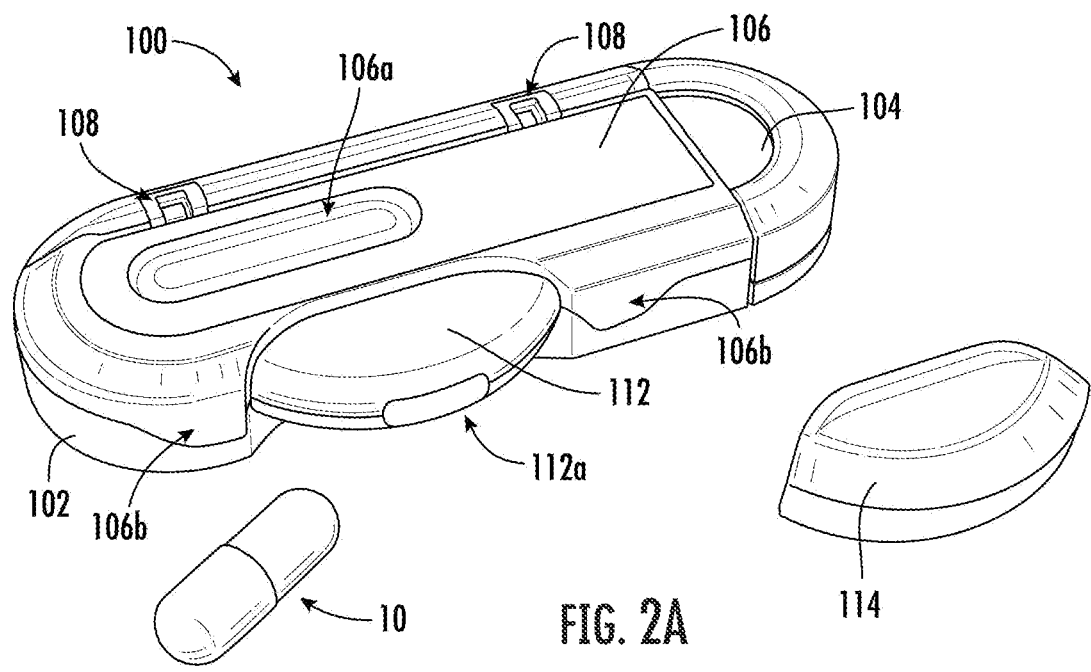
FIG. 2A is a top perspective view of the capsule inhaler of FIG. 1 with a cap removed.
Figure 2B:
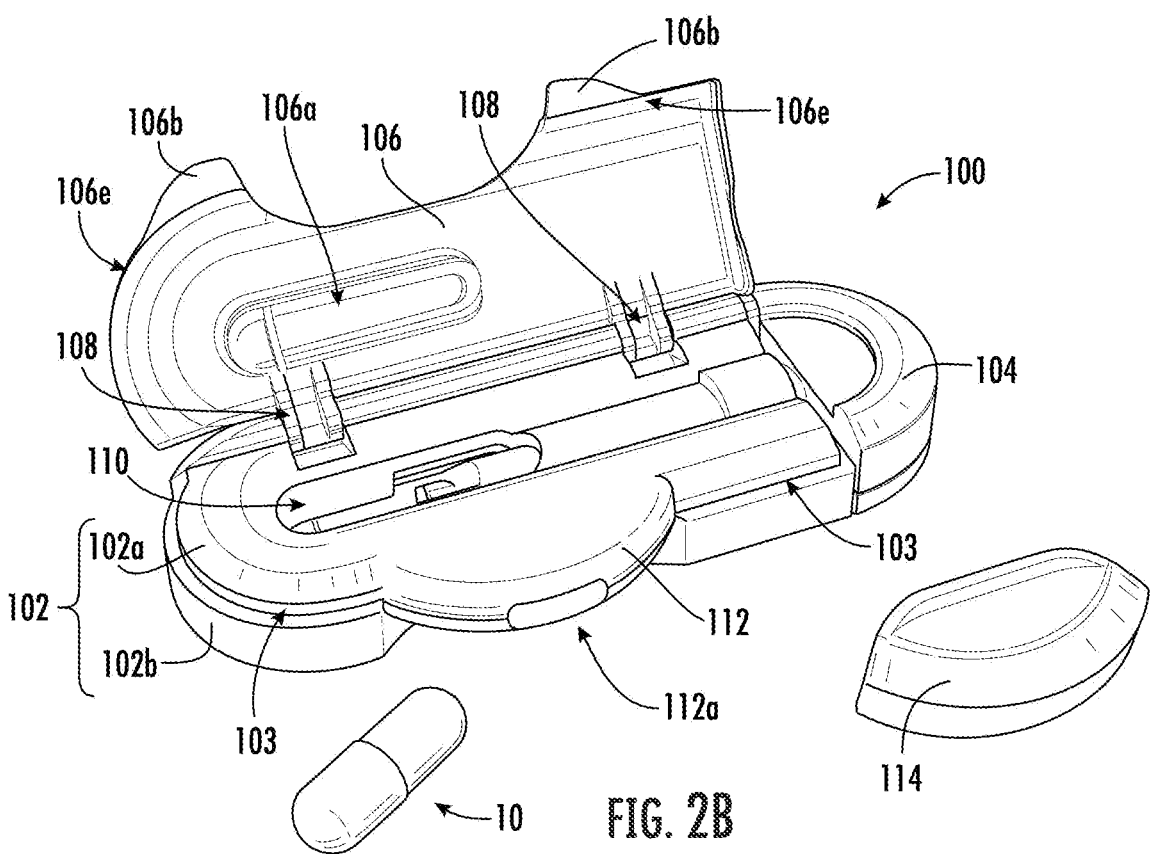

FIG. 2B is a top perspective view of the capsule inhaler of FIG. 1 with a cover opened.

Figure 2C:
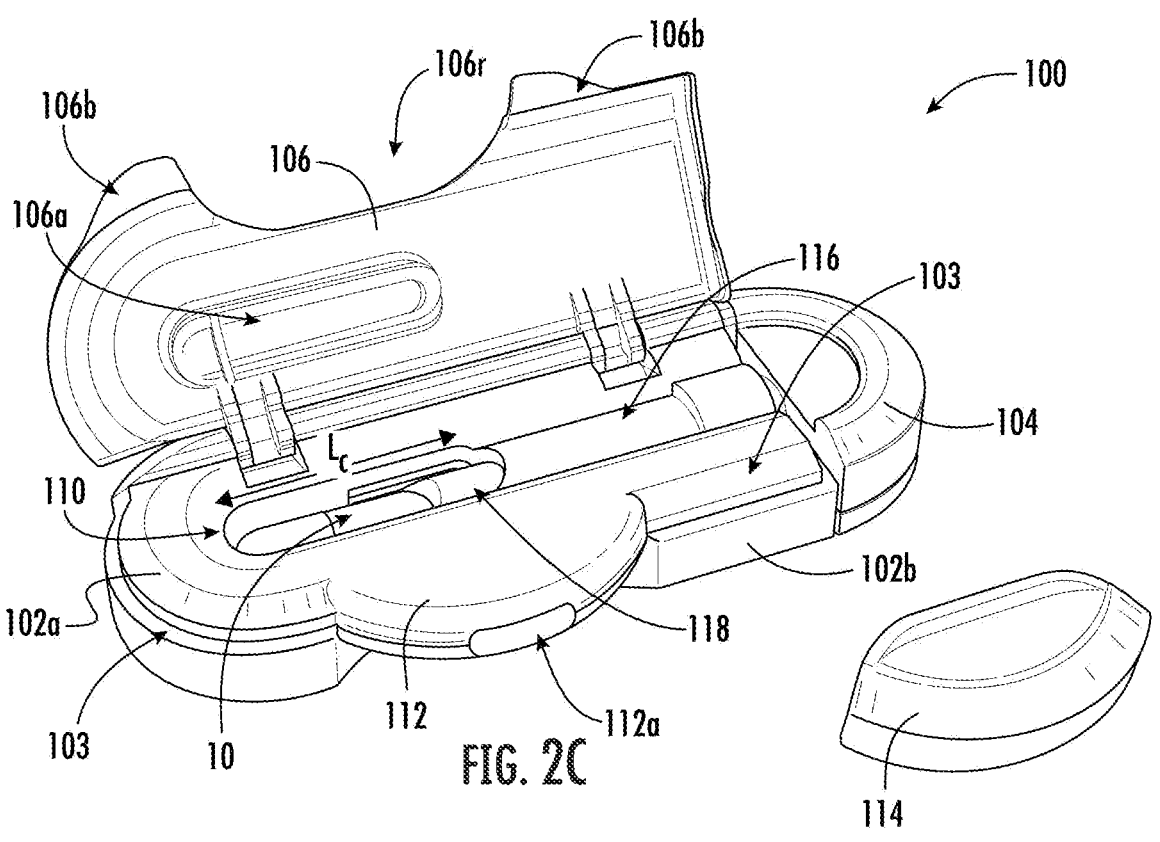

FIG. 2C is a top perspective view of the capsule inhaler of FIG. 1 with a capsule inserted into an inner cavity of the inhaler.

Figure 2D:
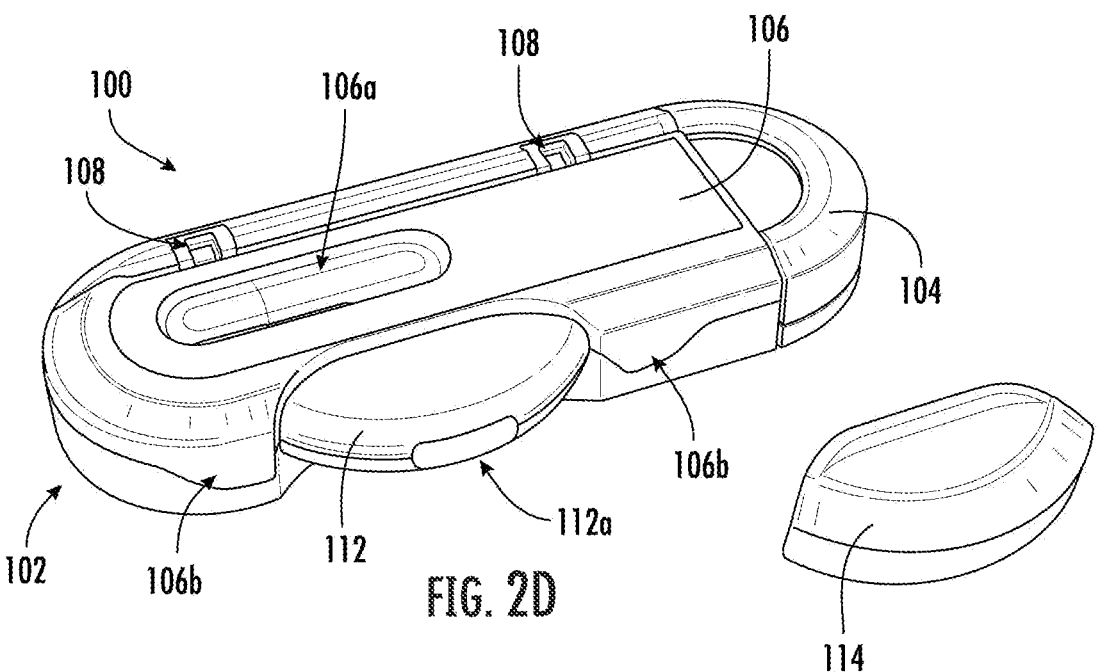

FIG. 2D is a top perspective view of the capsule inhaler of FIG. 2C with the cover closed.

Figure 2E:
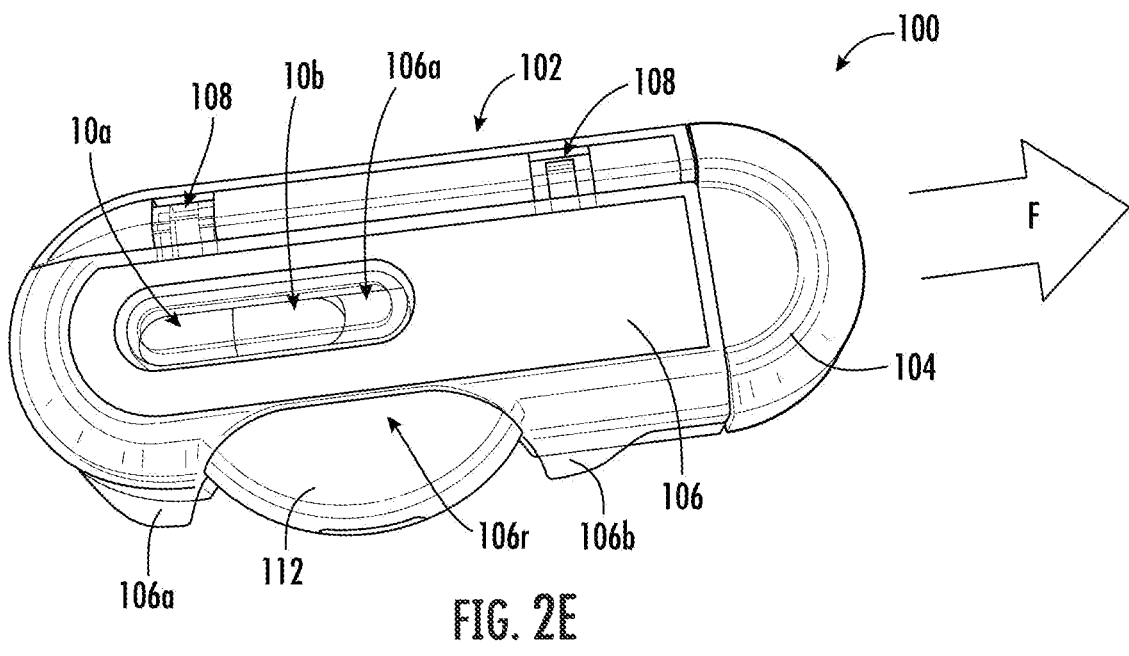

FIG. 2E is a top perspective view of the capsule inhaler of FIG. 2D showing the direction in which an actuator of the inhaler is pulled to open a capsule during use.

Figure 2F:
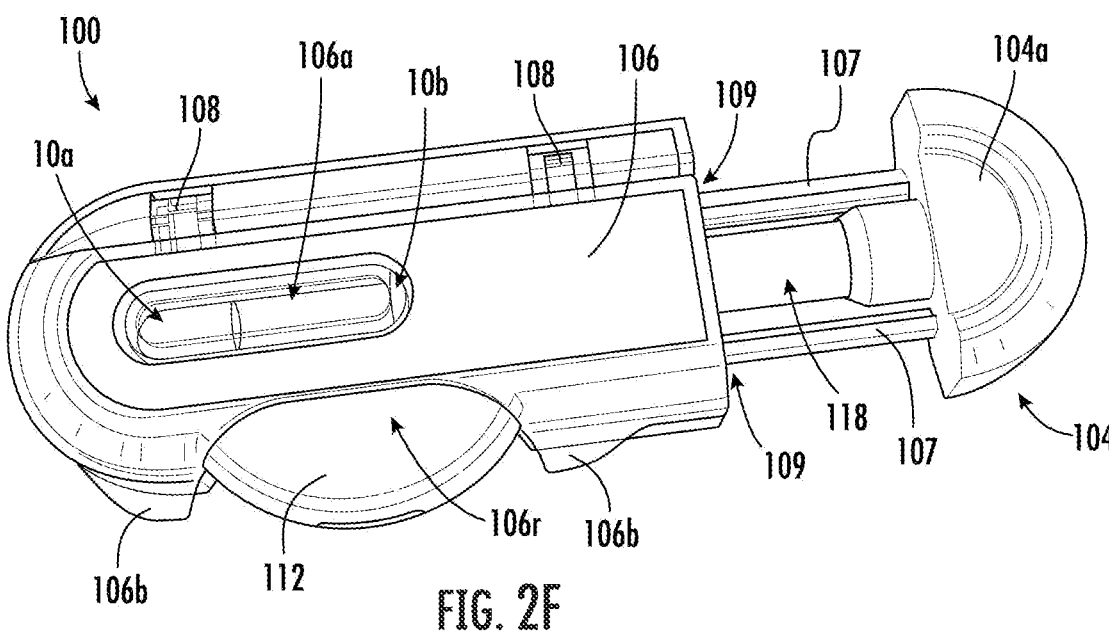

FIG. 2F is a top perspective view of the capsule inhaler of FIG. 2D with the actuator pulled to an open position which separates the capsule within the inhaler.

Figure 2G:
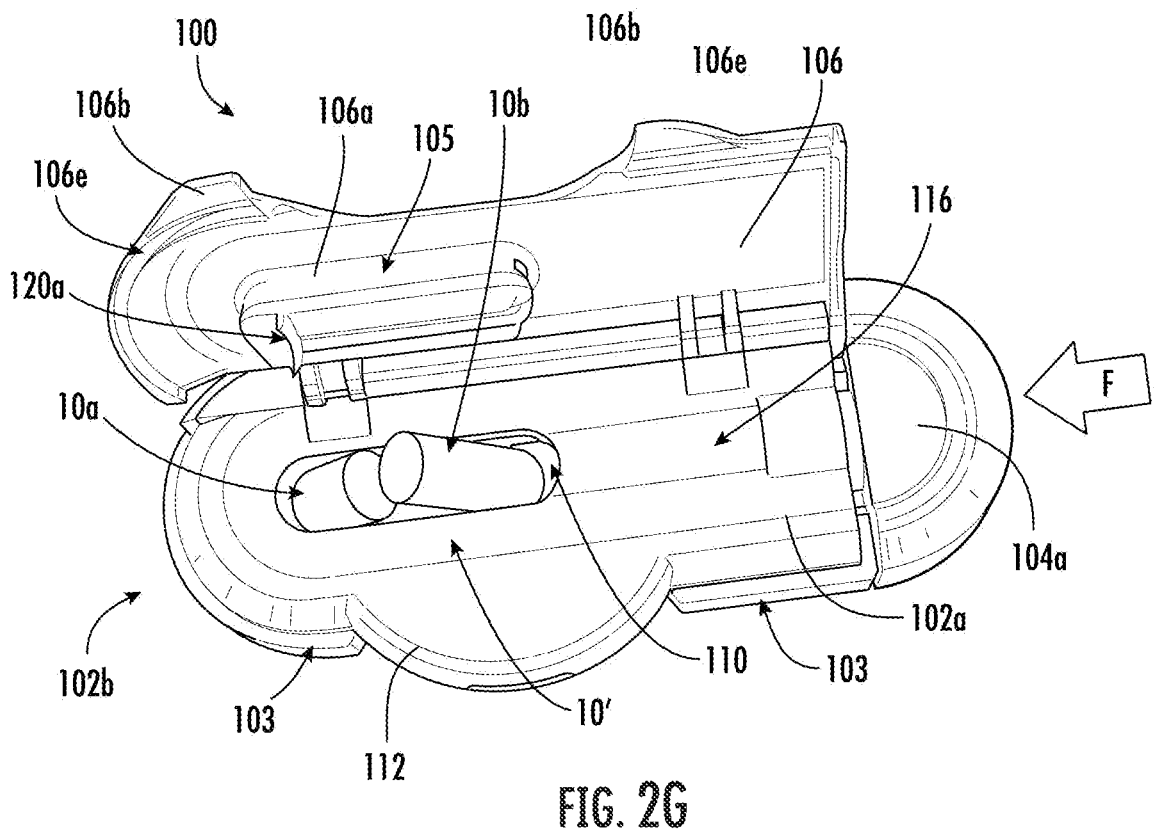

FIG. 2G is a top perspective view of the capsule inhaler of FIG. 2C with the actuator returned to a closed position and showing the separated, empty capsule configured for removal from the inhaler after use.

Figure 3A:
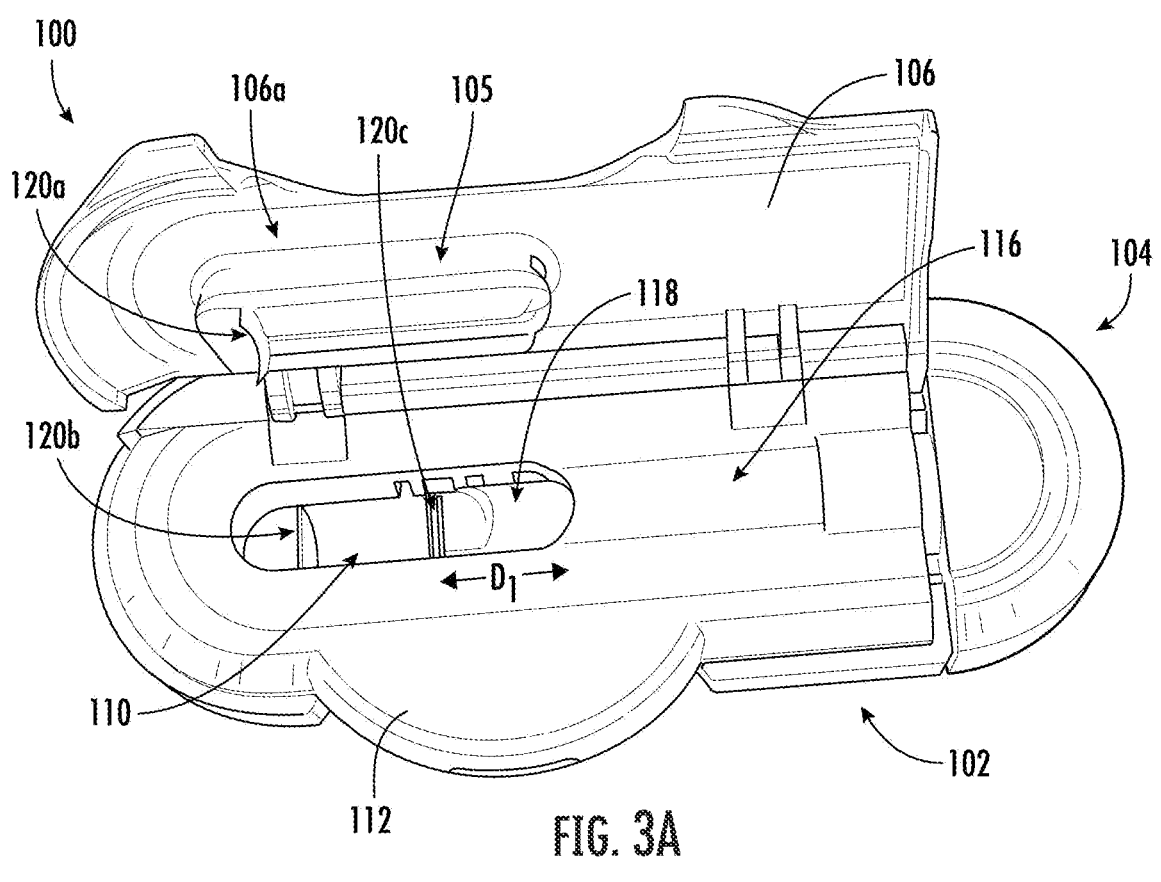
Figure 3B:
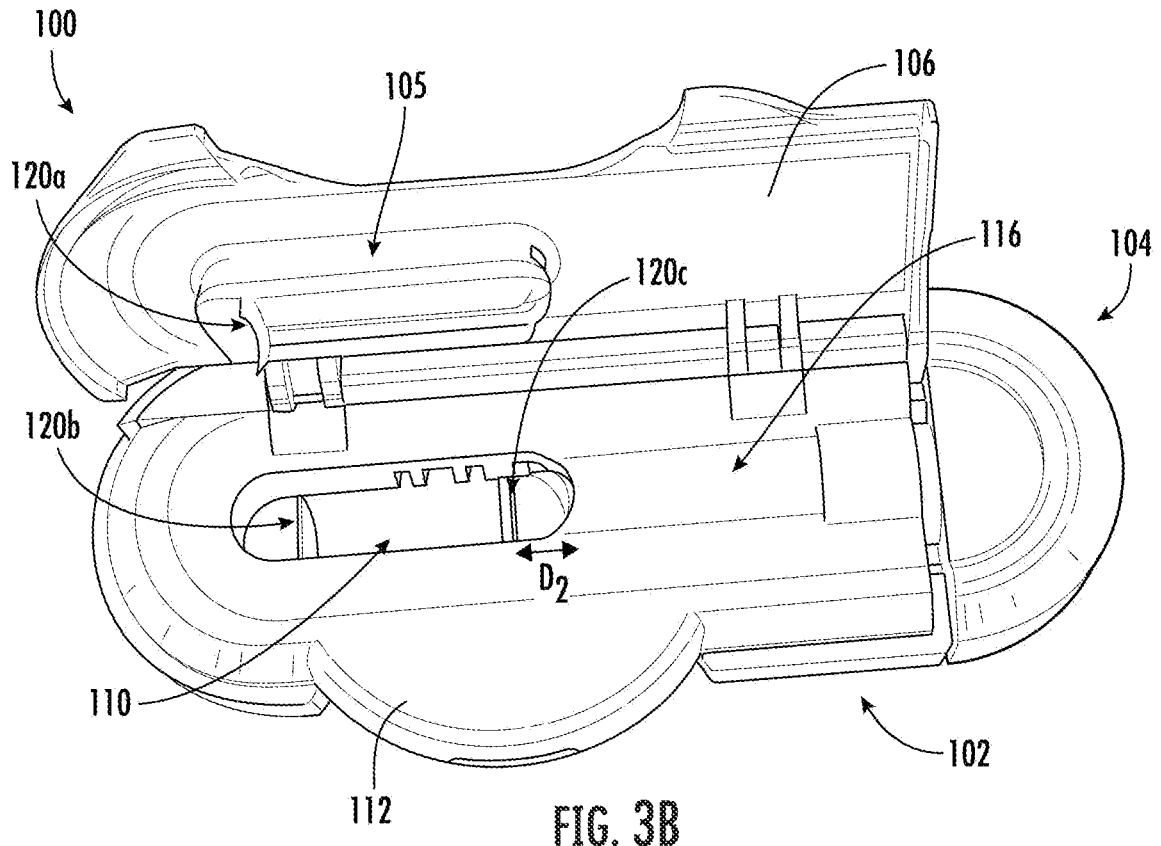
Figure 3C:
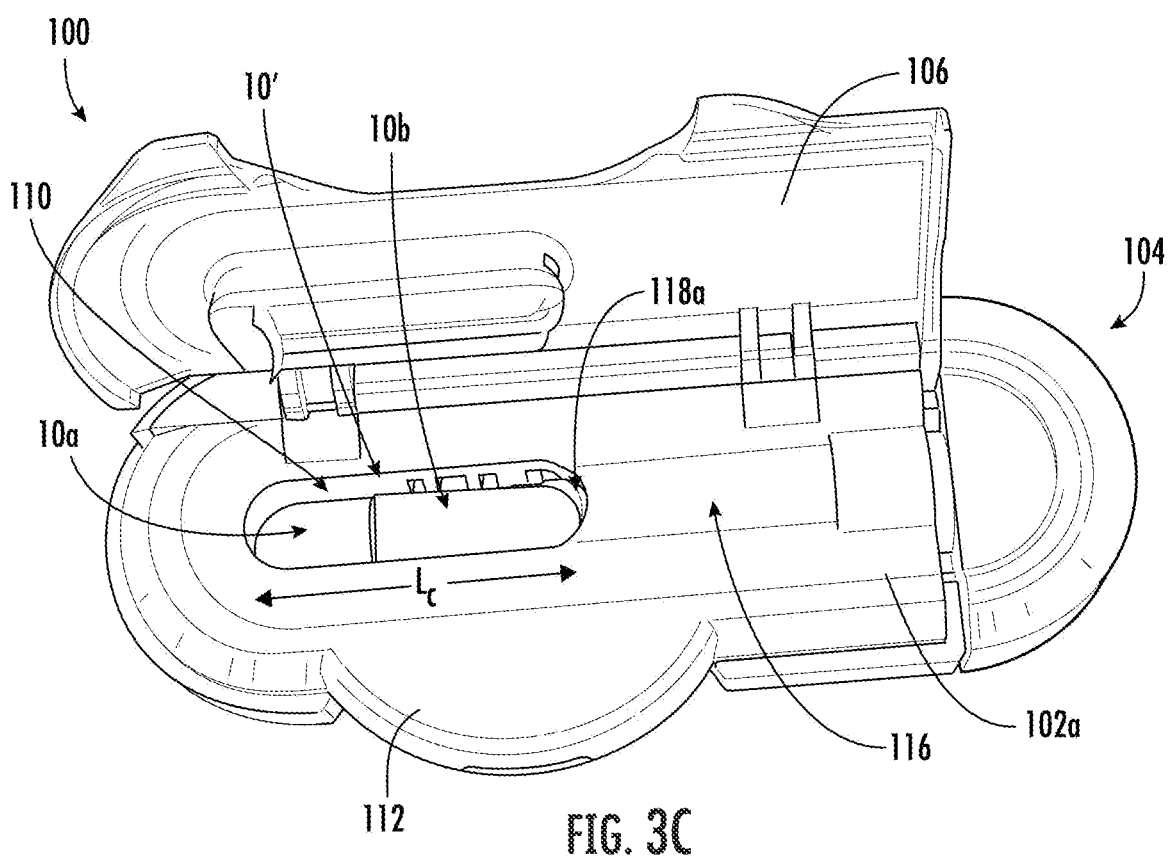

FIGS. 3A-3C are top perspective views of the capsule inhaler with the actuator of the capsule inhaler shown for illustrating features thereof according to embodiments of the present invention.

Figure 3D:
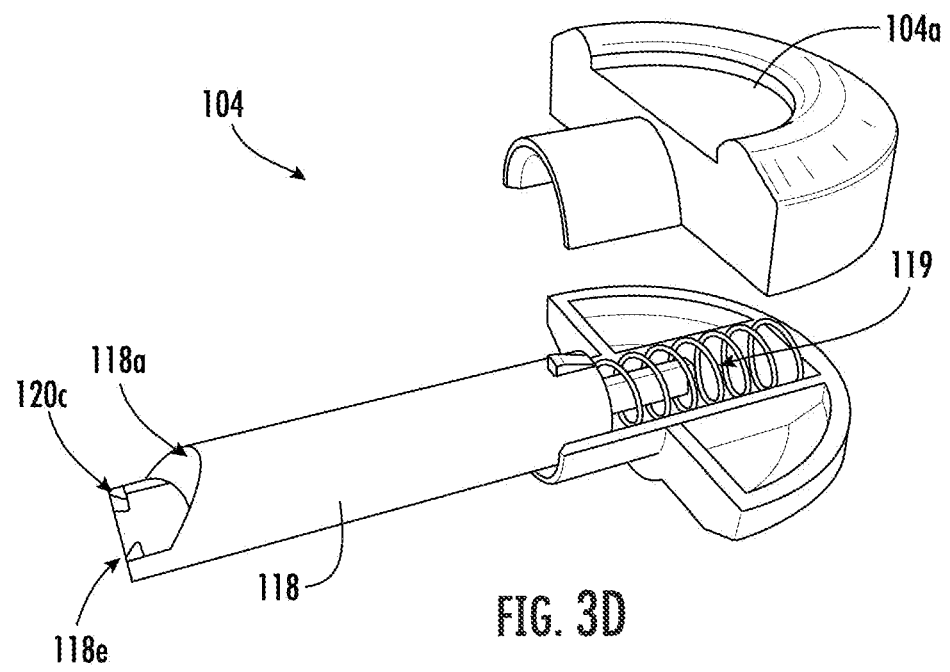

FIG. 3D is a partial exploded view of the actuator of the capsule inhaler of FIG. 1.

Figure 4A:
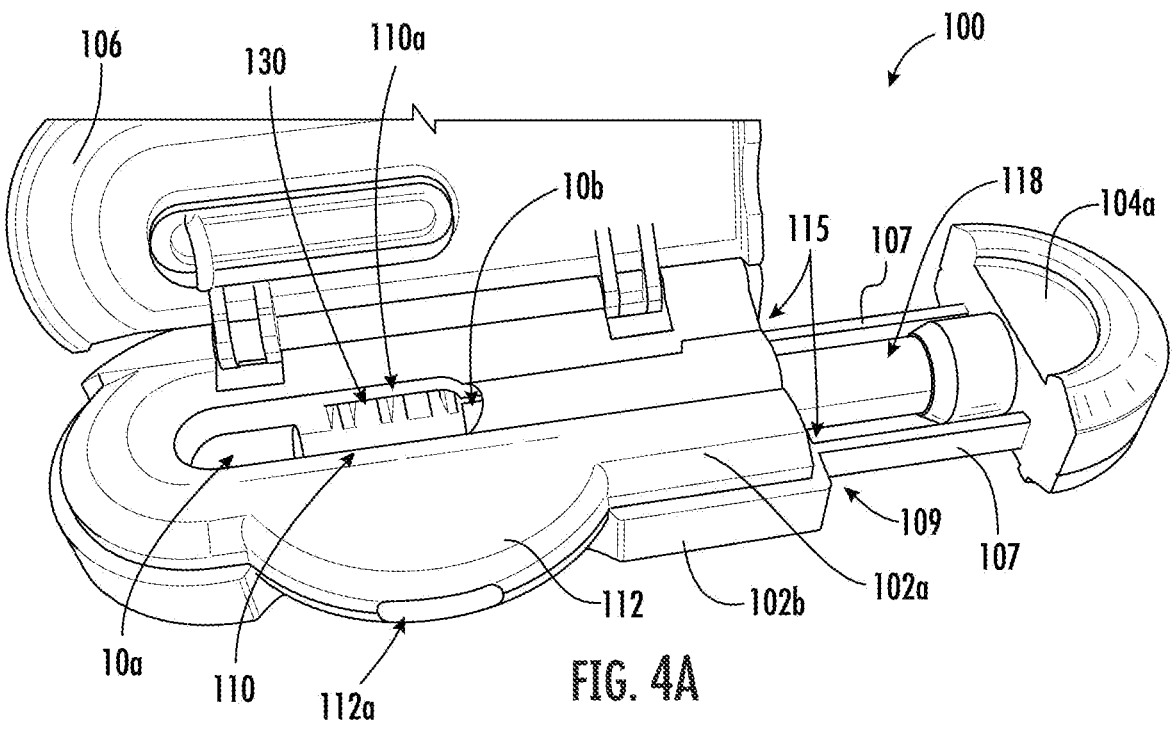

FIG. 4A is a top perspective view of the capsule inhaler of FIG. 1 shown with the actuator in an opened position and a separated capsule within the inner cavity of the inhaler.

Figure 4B:
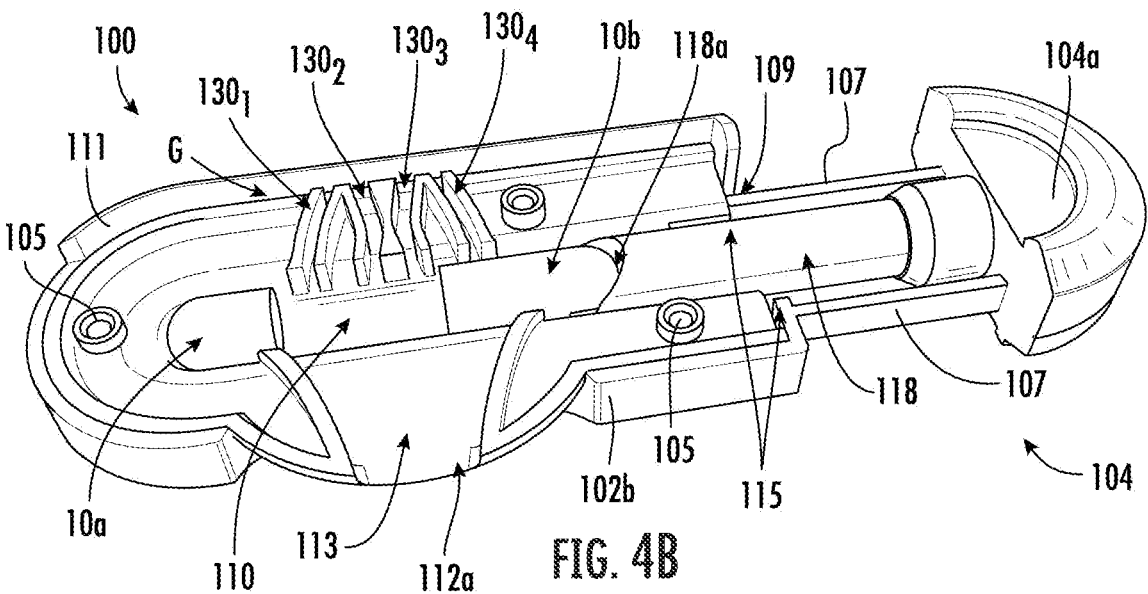

FIG. 4B is a top perspective view of the portion of the capsule inhaler of FIG. 4A without the cover and a portion of the main body to show example internal components of the inhaler according to embodiments of the present invention.

Figure 4C:
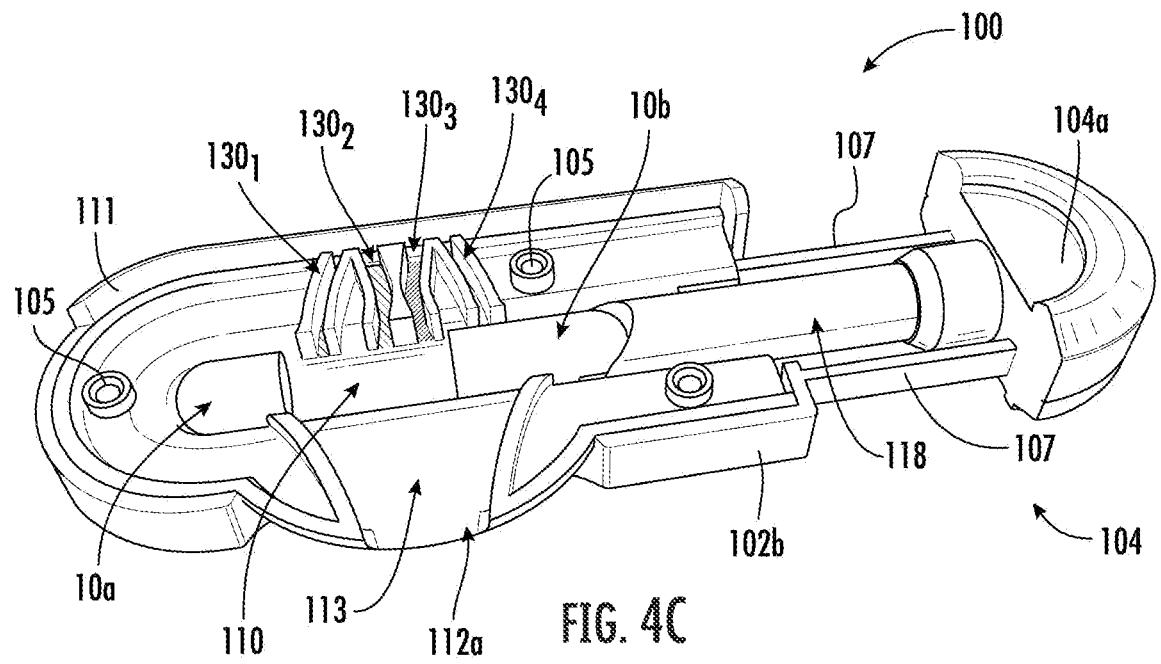

FIG. 4C is a top perspective view of the portion of the capsule inhaler of FIG. 4B shown with nozzle components provided by same according to embodiments of the present invention.

Figure 5A:
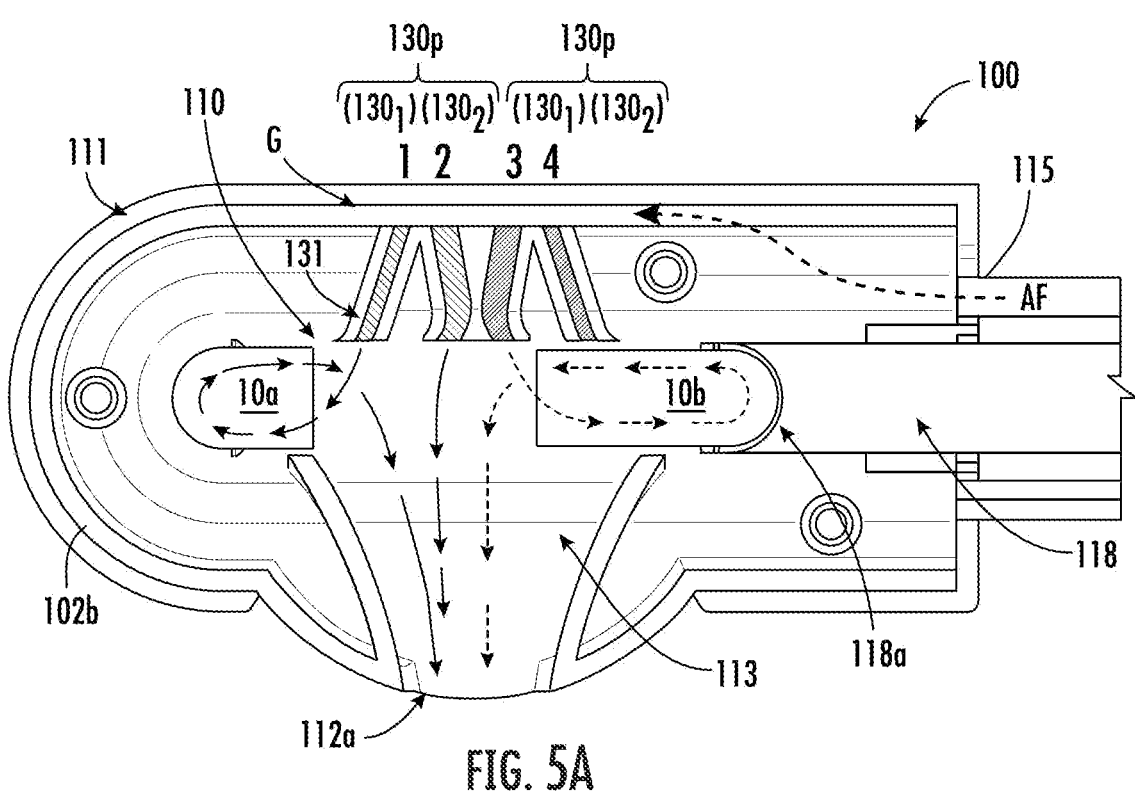

FIG. 5A is an enlarged top view of a portion of the capsule inhaler of FIG. 4B illustrating example air flow direction within the inhaler when a capsule is within the inner cavity oriented with a longer segment of the capsule adjacent to the right side of the inner cavity (closer to the actuator than the left side in the orientation shown) according to embodiments of the present invention.

Figure 5B:
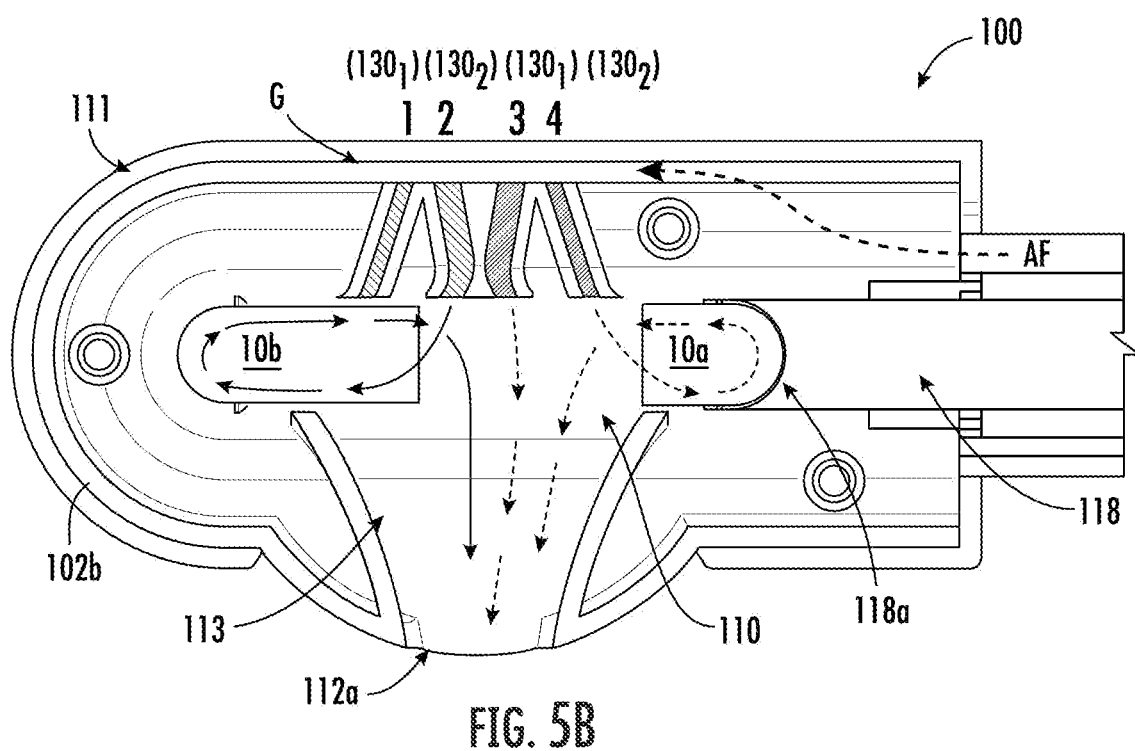

FIG. 5B is an enlarged top view of a portion of the capsule inhaler of FIG. 4B illustrating air flow within the inhaler when a capsule is oriented within the inner cavity with the longer segment of the capsule adjacent to the left side of the inner cavity according to embodiments of the present invention.

Figure 5C:
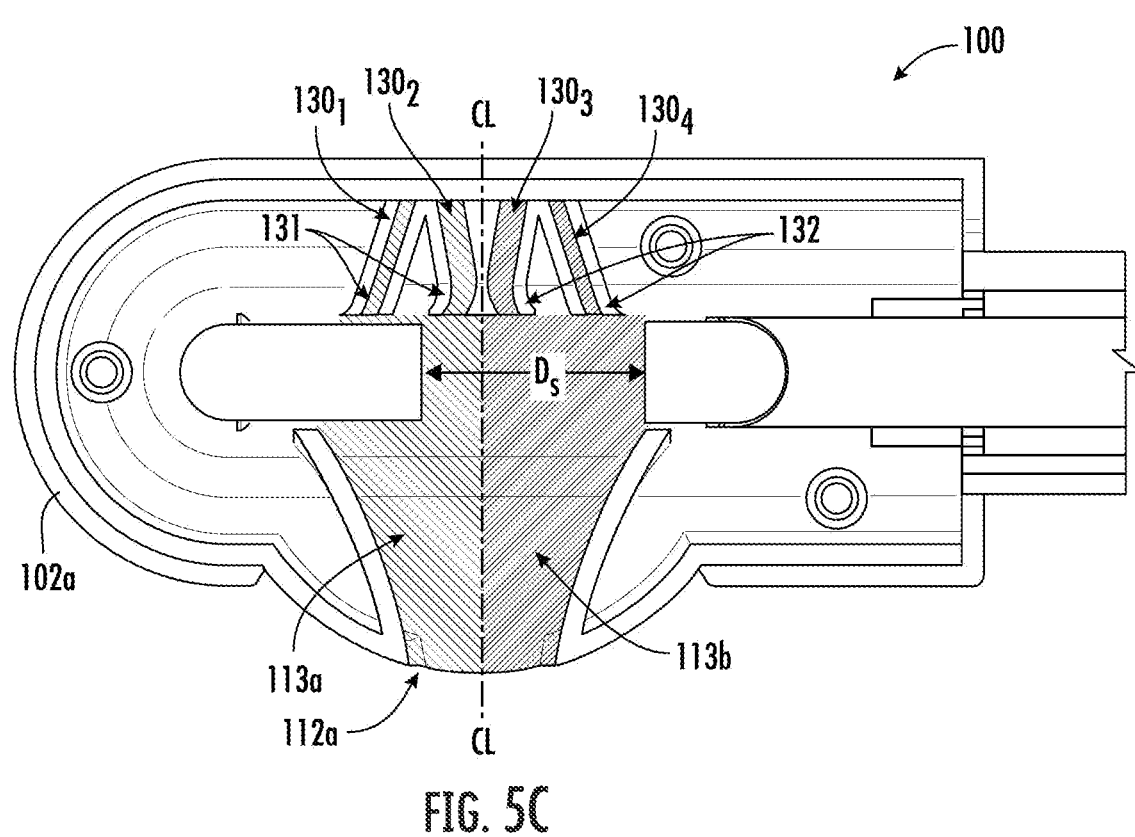

FIG. 5C is an enlarged top view of the capsule inhaler of FIG. 4B illustrating air flow provided by the left pair of nozzles and air flow provided by the right pair of nozzles that extend across the inner cavity while not crossing a center line (CL) extending between the two pairs of nozzles according to embodiments of the present invention.

Figure 5D:
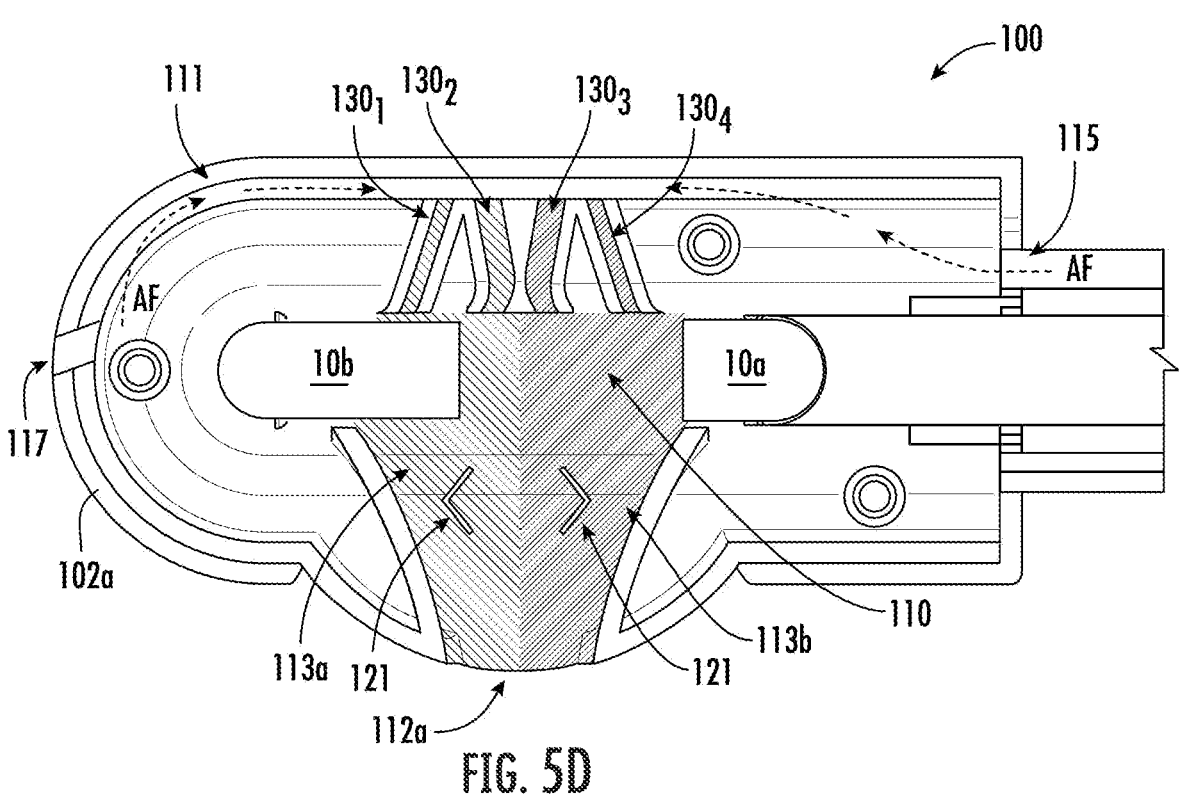

FIG. 5D is an enlarged top view of the capsule inhaler illustrating air flow provided through multiple spaced apart intake ports of the inhaler according to embodiments of the present invention.

Figure 6:
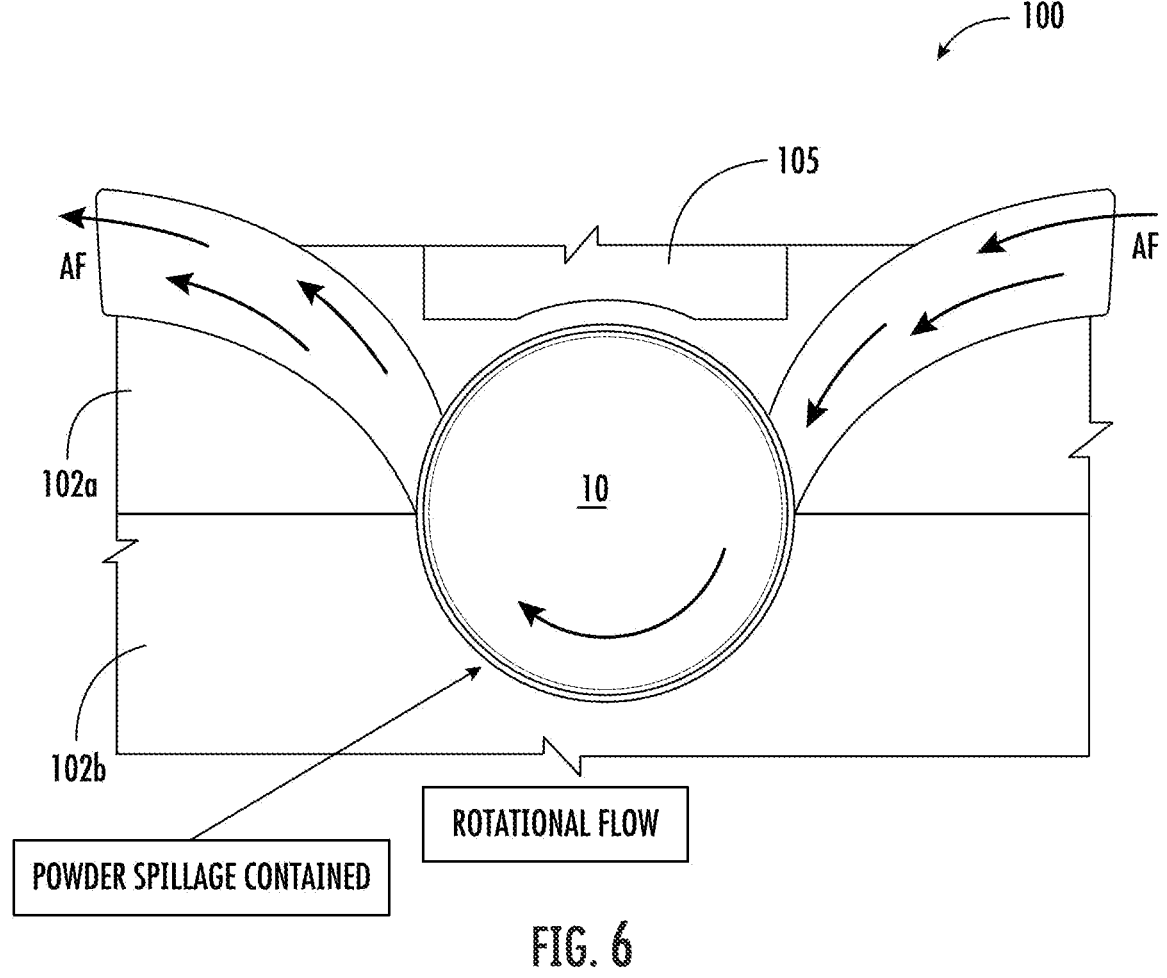

FIG. 6 is a partial end section view of the inhaler illustrating the partially rotational air flow within the inhaler to flowably entrain dry powder out from the capsule according to some embodiments of the present invention.

Figure 7A:
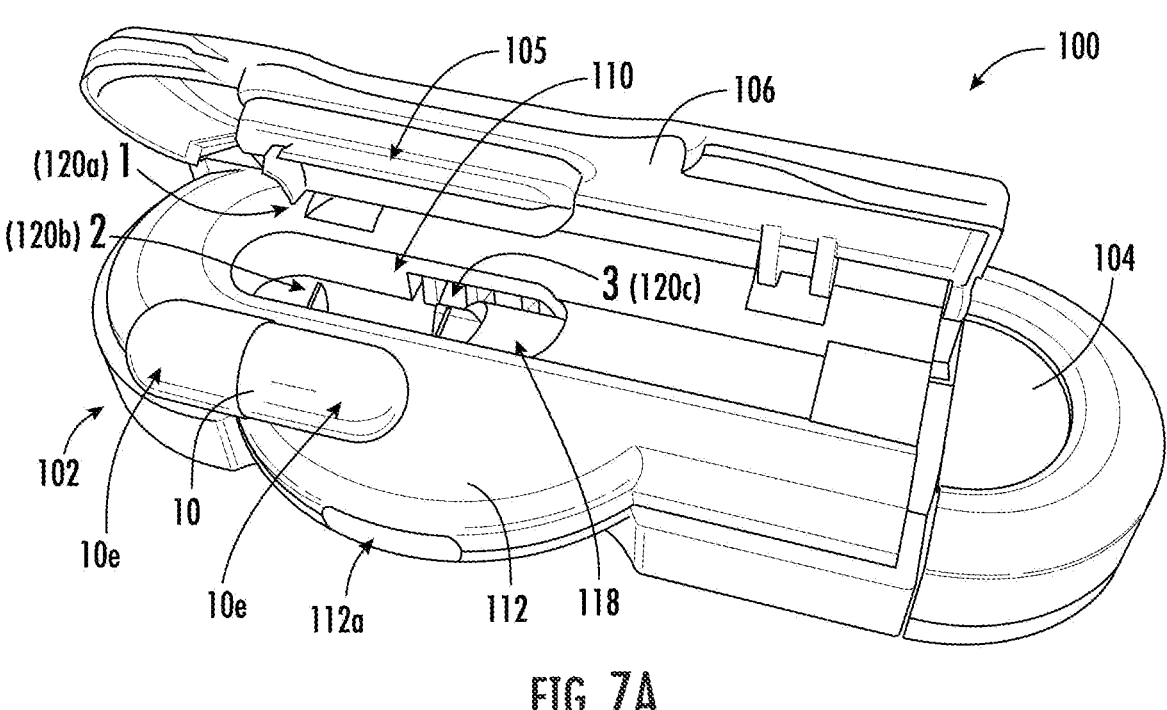

FIG. 7A is a top perspective view of the capsule inhaler of FIG. 1 illustrating gripping features within the inhaler according to embodiments of the present invention.

Figure 7B:
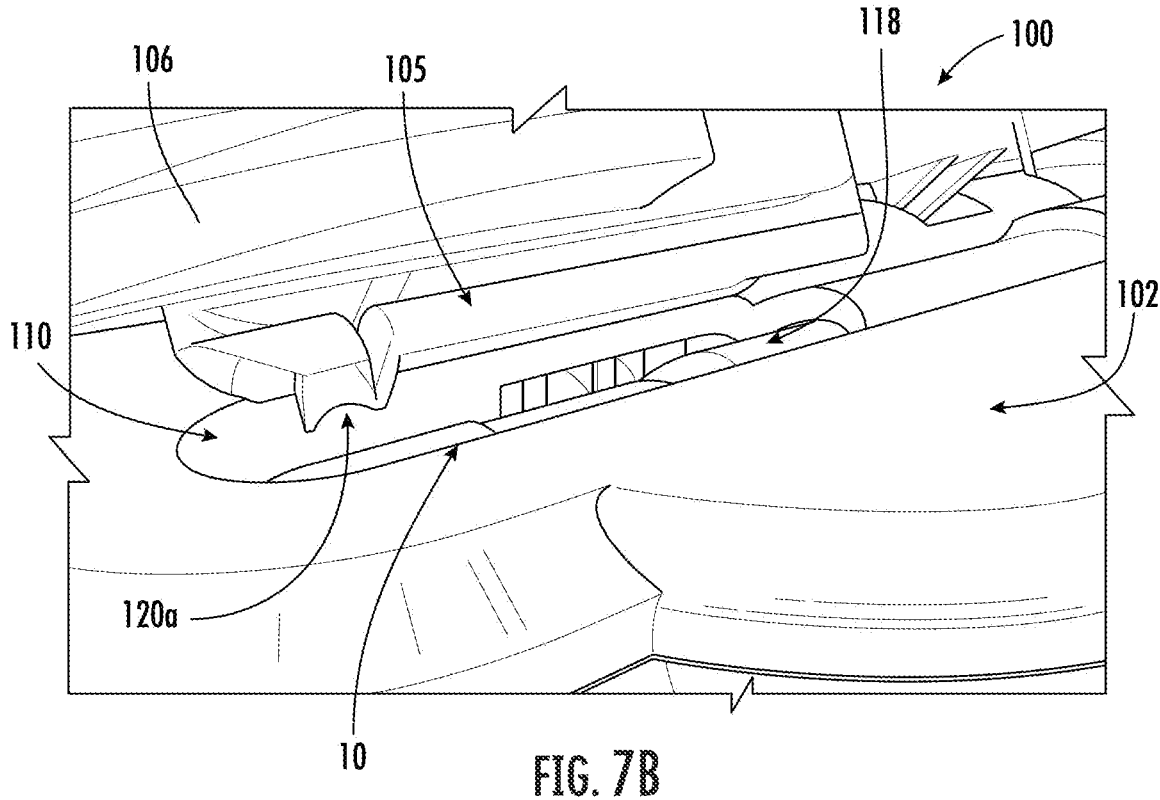

FIG. 7B is an enlarged view of the capsule inhaler of FIG. 7A showing a gripping feature on the top cover.

6

Figure 8A:
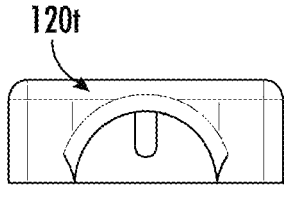
Figure 8B:
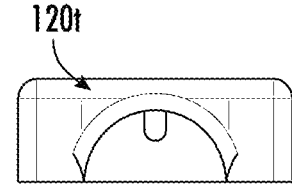
Figure 8C:
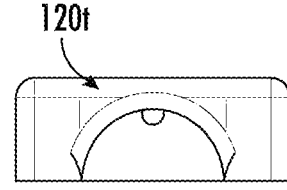
Figure 8D:
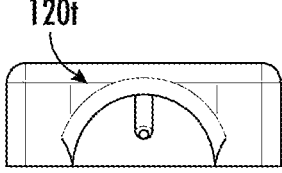
Figure 8E:
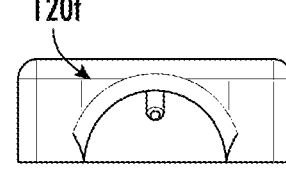
Figure 8F:
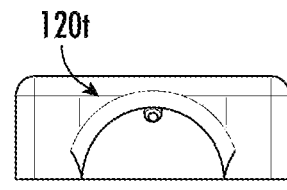
Figure 8G:
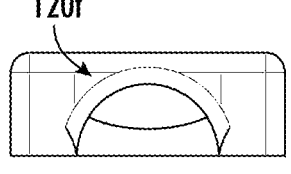
Figure 8H:
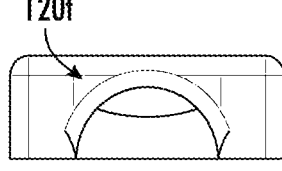
Figure 8I:
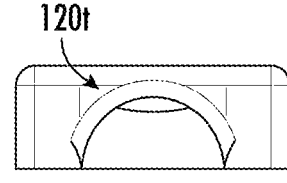
Figure 8J:
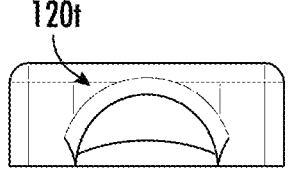
Figure 8K:
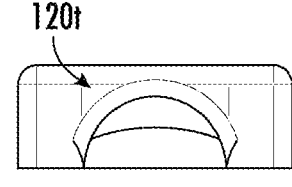
Figure 8L:
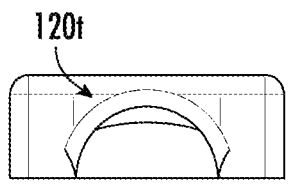
Figure 8M:
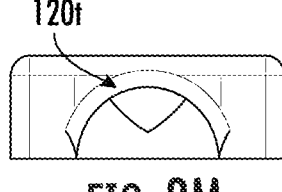
Figure 8N:
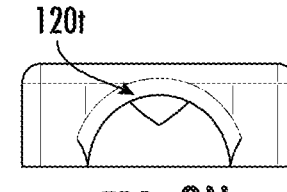
Figure 8O:
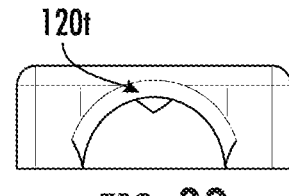
Figure 8P:
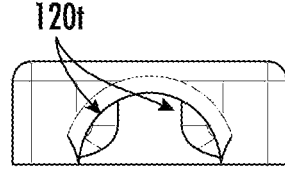
Figure 8Q:
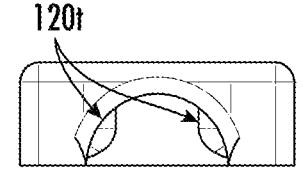
Figure 8R:
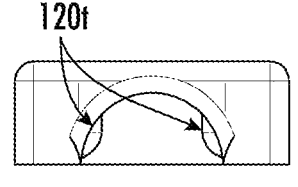

FIGS. 8A-8R illustrate different gripping feature geometries that may be utilized in the capsule inhaler according to embodiments of the present invention.

DETAILED DESCRIPTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In the figures, certain layers, components, or features may be exaggerated for clarity, and broken lines illustrate optional features or operations unless specified otherwise. The terms "FIG." and "Fig." are used interchangeably with the word "Figure" in the application and/or drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer, or section. Thus, a first element, component, region, layer, or section discussed below could be termed a second element, component, region, layer, or section without departing from the teachings of the present invention. The sequence of operations (or steps) is not limited to the order presented in the claims or figures unless specifically indicated otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used.

Referring now FIGS. 1-7B, a capsule inhaler 100 is illustrated. The capsule inhaler 100 of the present invention is for use with a capsule 10 containing a dry powder formulation (or agent) such as a dry powder pharmaceutical or nutraceutical. The capsule 10 may comprise two detachable cylindrical segments 10a, 10b releasably secured together with a dry powder formulation/agent (e.g., dry powder pharmaceutical or nutraceutical) contained therein (FIG. 1). In some instances, one of the segments 10a of the capsule 10 may be shorter than the other segment 10b (see, e.g., FIG. 2G, FIG. 3C, FIGS. 4B-4C, and FIGS. 5A-5C). The closed end of each segment 10e can be more rigid than a respective open end. The segments 10a, 10b can be secured together via an interference fit.

As shown in FIG. 1, the inhaler 100 includes a main body 102 and an actuator 104 coupled to the main body 102. As discussed in further detail below, according to embodiments of the present invention, during use of the inhaler 100, the actuator 104 is configured to separate the two segments 10a, 10b of the capsule 10 (i.e., open the capsule 10), thereby allowing a user (i.e., patient or subject) to inhale the dry powder pharmaceutical or nutraceutical contents of the capsule 10. In some embodiments, the subject is a human being.

The inhaler 100 can have a length $L_i$, a width $W_i$, and a height (or thickness) $H_i$. The length $L_i$ can be greater than the height $H_i$ and the width $W_i$. The length can be at least 2× greater, typically 3×-6× greater, than the width $W_i$. The main body 102 can have planar primary elongate outer surfaces and can be configured to be held in a pocket of a garment of a user, such as a shirt, pants, or jacket. In some embodiments, the inhaler 100 may have a length $L_i$ that is between about 3 inches and about 4 inches. For example, in some embodiments, the inhaler 100 may have a length $L_i$ of 3.5 inches. In some embodiments, the inhaler 100 may have a width W; that is between about 1 inch and about 2 inches. For example, in some embodiments, the inhaler 100 may have a width $W_i$ of 1.5 inches. In some embodiments, the inhaler 100 may have a height $H_i$ that is between about 0.4 inches and about 0.8 inches. For example, in some embodiments, the inhaler 100 may have a height $H_i$ of 0.65 inches.

The inhaler 100 can be tunable for different uses of different size capsules 10 and/or different pharmaceutical and/or different nutraceutical formulations in such capsules 10. The inhaler 100 can be sized and configured to receive a size 0 capsule 10. The inhaler 100 can be sized and configured to receive a size 3 capsule 10. Exemplary capsule sizes and dimensions are shown in Table 1 (ACG Capsules, Mumbai, India).

In some embodiments, capsules 10 having an overall closed length $L_p$ between about 15.8 mm (±0.4 mm) (e.g., for size 3 capsules) and about 21.4 mm (±0.4 mm) (e.g., size 0 capsule) may be used with the inhaler 100 of the present invention. In some embodiments, the inhaler 100 may be formed of a polymeric material (e.g., plastic). In some embodiments, the inhaler 100 may be formed via injection molding. In some embodiments, the inhaler 100 may be molded from biodegradable plastics or formed cardboard.

Referring to FIGS. 2A-2G, the main body 102 of the inhaler 100 may comprise a first portion 102a and second portion 102b. In the orientation shown, the first portion 102a is a top portion and the second portion 102b is a bottom portion. The first and second portions 102a, 102b of the main body 102 may be secured together via one or more securing members 105, such as, cooperating snap-fit features (see, e.g., FIGS. 4B-4C).

The inhaler 100 comprises an inner cavity 110. The inner cavity 110 is sized and configured to receive a capsule 10. In some embodiments, the inner cavity 110 has a length $L_c$ extending in the length direction of the inhaler 100 that can be between about 0.85 inches and about 1.25 inches (see, e.g., FIG. 2C and FIG. 3C). For example, in some embodiments, the inner cavity 110 has a length $L_c$ of about 0.93 inches (e.g. for size 3 capsules). In other embodiments, the inner cavity 110 has a length of about 1.18 inches (e.g., for size 0 capsules). In some embodiments, the length of the inner cavity 110 is greater than the length of the capsule 10 (i.e., $L_e > L_p$) by about 10%-30%.

In some embodiments, the first and second portions 102a, 102b cooperate to define the inner cavity 110. In other embodiments, the main body 102 may be unitary or monolithic with the inner cavity 110 formed therein.

In some embodiments, the inner cavity 110 of the inhaler 100 may comprise one or more gripping features 120b, optionally comprising one or more teeth 120t (see, e.g., FIGS. 3A-3B, FIGS. 7A-7B, and FIGS. 8A-8R). As discussed in further detail below, the one or more gripping features 120b are configured to engage the capsule 10 and assist the actuator 104 in separating (i.e., opening) the capsule 10 within the inner cavity 110 of the inhaler 100 (see also, e.g., FIGS. 8A-8R) without puncturing the capsule 10.

As shown in FIG. 1 and FIGS. 2A-2D, the main body 102 of the inhaler 100 further includes a mouth section 112 having an aperture 112a. The mouth section 112 can be arcuate and can project outwardly from the main body 102. The aperture 112a is an external port that merges into a laterally extending channel 113 (FIG. 4B and FIGS. 5A-5C) that extends into the inner cavity 110. As discussed in further detail below, during use of the inhaler 100, the user (e.g., a patient or subject) will place their mouth about the mouth section 112 and over the aperture 112a to inhale and receive the contents of the capsule 10 (i.e., via inhalation). As shown in FIG. 1, when the inhaler 100 is not being actively used, a cap 114 may be placed over the mouth section 112 (and aperture 112*a*). The cap 114 may help to prevent dust, dirt, lint, etc. from entering the channel 113 and inner cavity 110 of the inhaler 100. A tether may be used to connect the cap 114 to the main body 102 of the inhaler 100 (not shown). Other cap retention configurations of the inhaler 100 may be used to hold the cap 114 when disengaged from the mouth section 112 (not shown). In some embodiments, the inhaler 100 may be sealed in an overwrap (e.g., foil or plastic) or other packaging (not shown) and used as a one-time disposable delivery system. For example, the user opens the packaging, uses the inhaler 100 and throws away or otherwise disposes of the inhaler 100.

As shown in FIG. 2C, FIG. 2G, and FIGS. 3A-3D, the main body 102 of the inhaler 100 may further include a second channel 116 extending in the length direction from the inner cavity 110 toward the actuator 104. The channel 116 is sized and configured to slidably receive an elongate member 118 (FIGS. 4C and 7A) of the actuator 104.

The actuator 104 of the inhaler 100 may include a head portion 104*a* coupled to the elongate member 118 (see, e.g., FIG. 2F). The head portion 104*a* provides a location for the user to grip and move (i.e., pull/push) the actuator 104. In some embodiments, the elongate member 118 may include a spring-loaded assembly 119 which allows the elongate member 118 to be resiliently biased and movable between extended and retracted positions (see, e.g., FIG. 3D). The spring-loaded assembly 119 also may help to bias the elongate member 118 within the channel 116 of the main body 102 and against a facing end 10*e* of the capsule 10 within the inner cavity 110 of the inhaler 100. The biased configuration of the elongate member 118 may help to prevent the capsule 10 from being crushed or jammed within the inhaler 100 by the elongate member 118.

Referring to FIGS. 3A-3D, in some embodiments, one or more gripping features 120*c*, optionally comprising one or more teeth 120*t*, may reside at the end portion 118*e* of the elongate member 118. The gripping features 120*c* can at least partially extend into the inner cavity 110 of the inhaler 100 and couple to a corresponding end portion 10*e* of one segment 10*a*, 10*b* of the capsule 10 (see, e.g., FIGS. 3A-3B). The end portion 118*e* of the elongate member 118 may comprise an arcuate section 118*a* that corresponds to the shape/end profile of the capsule 10 (see, e.g., FIGS. 3C-3D, FIG. 4B, and FIGS. 5A-5B). The one or more gripping features 120*c* of the elongate member 118 of the actuator 104 are configured to engage the end portion of the capsule 10 and assist in separating the capsule 10 into the segments 10*a*, 10*b* within the inner cavity 110 of the inhaler 100 (see also, e.g., FIGS. 7A-7B and FIGS. 8A-8R). As discussed in further detail below, the inhaler 100 (i.e., actuator 104) is configured to separate the capsule 10 such that adjacent ends of the separated segments 10*a*, 10*b* are spaced apart a distance D*s* to provide efficient and consistent dry powder output, e.g., pharmaceutical or nutraceutical (e.g., dry powder) dispersion, emittance and deaggregation (see, e.g., FIG. 5C).

Referring to FIGS. 3A-3C, and discussed in further detail below, once a capsule 10 is separated within the inhaler 100, the two segments 10*a*, 10*b* typically cannot be reassembled, resulting in the capsule 10 occupying a space that is longer than its initial length L*p*. FIG. 3A shows the elongate member 118 of the actuator 104 in a first position whereby the elongate member 118 extends a first distance D₁ into the inner cavity 110, i.e., biased into a position to receive intact capsule 10. FIGS. 3B-3C show the elongate member 118 of the actuator 104 in a second position in which the elongate member 118 extends a second (shorter) distance D₂ into the inner cavity 110, i.e., to accommodate the separated capsule 10.

Referring to FIG. 2F and FIGS. 4A-4C, in some embodiments, the actuator 104 may further include a pair of guide rails 107. As shown, the guide rails 107 are coupled to the head portion 104*a* of the actuator 104 and are configured to slide within corresponding recesses 109 in the main body 102. The guide rails 107 may help to balance, position and/or guide the elongate member 118 to facilitate sliding operation, such as when being moved from an opened or closed position by a user (see, e.g., FIGS. 2E-2G). The guide rails 107 may also provide structural support to the actuator 104.

As shown, the inhaler 100 further includes a cover 106 that is pivotably coupled to the main body 102. As shown in FIGS. 2A-2F, the cover 106 may be pivotably coupled to the main body 102 via at least one hinge 108, shown as a pair of hinges 108, which allows a user to move the cover 106 from a closed position (see, e.g., FIG. 2A and FIGS. 2D-2F) to an opened position (FIGS. 2B-2C) and vice versa. In some embodiments, the cover 106 may comprise a visually transmissive section (or window) 106*a* which allows the user to see into the inner cavity 110 of the inhaler 100 when the cover 106 is in a closed position (see, e.g., FIG. 2A and FIGS. 2D-2F). In some embodiments, at least a portion of the visually transmissive section 106*a* may cover the inner cavity 110. Referring to FIG. 2G and FIG. 4A, an internal wall or surface 105 of the visually transmissive section 106*a* may include one or more gripping features 120*a*, such as teeth 120*t* (see also, e.g., FIGS. 8A-8R), that are configured to engage the capsule 10 and assist in separating the capsule 10 within the inner cavity 110 of the inhaler 100.

Referring to FIGS. 2A-2G, in some embodiments, the cover 106 may include one or more flanged edges 106*b* extending outwardly from the cover 106 opposite to the hinges 108. When the cover 106 is in a closed position, the flanged edges 106*b* may reside on either side of the mouth section 112 (see, e.g., FIG. 2A and FIGS. 2D-2F). The flanged edges 106*b* provide a location for a user to grip the cover 106 when pivoting the cover 106 from an opened or closed position. In some embodiments, the cover 106 may also comprise a recessed area 106*r* which corresponds to the mouth section 112. As shown in FIGS. 2E-2F, the recessed area 106*r* allows the cover 106 to be closed while the mouth section 112 remains externally accessible, e.g., without obstructing the mouth section 112 from use. The cover 106 is shown as a top cover but the inhaler 100 can be configured so that the cover 106 is a bottom cover.

Referring to FIGS. 2B-2C, in some embodiments, the cover 106 may further include a beveled edge 106*e* that is configured to engage with the main body 102 to secure/hold the cover 106 in a closed position until a user opens the cover 106. In some embodiments, the main body 102 may include a shoulder or ledge 103 that is configured to engage the beveled edge 106*e* of the cover 106. For example, in some embodiments, the first portion 102*a* of the main body 102 may be slightly smaller in size than the second portion 102*b* of the main body 102. As shown in FIG. 2B, when the first and second portions 102*a*, 102*b* are secured together, the difference in sizes may create the ledge 103 that couples to the beveled edge 106*e* of the cover 106.

According to embodiments of the present invention, to operate the capsule inhaler 100, a user removes the cap 114 from the mouth section 112 (FIG. 2A). Next, the cover 106 is pivoted (via hinges 108) to an open position to provide the user access to the inner cavity 110 of the inhaler 100 (FIG. 2B). A capsule 10 is then inserted into the inner cavity 110 (FIG. 2C). As discussed in further detail below, when inserted into the inner cavity 110, the inhaler 100 is configured to operate in the same manner irrespective of which orientation a user inserts the capsule 10 within the inner cavity 110 (i.e., the capsule 10 may be oriented with the shorter segment 10a of the capsule 10 on the left side of the inner cavity 110 and the longer segment 10b of the capsule 10 on the right side of the inner cavity 110 or the reverse).

As shown in FIG. 2D, once the capsule 10 is inserted within the inner cavity 110, the cover 106 is closed, thereby securing the capsule 10 within the inhaler 100. When the capsule 10 is inserted into the inner cavity 110, one segment, either 10a or 10b of the capsule 10, will be in contact with the one or more gripping feature 120b, optionally tooth or teeth 120t, of the inner cavity 110 and the other segment 10a or 10b will be in contact with the one or more gripping features 120c of the elongate member 118 (see also, e.g., FIG. 7A). As the cover 106 is moved to a closed position, the one or more gripping feature 120a of the inner surface 105 contacts the same segment 10a or 10b as the one or more gripping features 120b of the inner cavity 110 (e.g., segment 10a as shown in FIG. 2E), thereby securing the segment 10a or 10b of the capsule 10 between cooperating gripping features 120a, 120b (see also, e.g., FIG. 7B). Typically, the ends of the capsule 10 are more rigid compared to the open adjacent ends at a medial portion of the capsule 10. In some embodiments, the one or more gripping features 120a, 120b, 120c may be positioned to engage the capsule 10 close to its more rigid ends 10e which may deform the outer wall shapes thereat but help to prevent the gripping features 120a, 120b, 120c from puncturing the capsule 10.

When the user is ready to inhale the contents of the capsule 10 (e.g., the dry powder pharmaceutical or nutraceutical) from the inhaler 100, the user places their mouth about the mouth section 112 of the inhaler 100, grips the actuator 104 (e.g., via the actuator head 104a) and pulls the actuator 104 longitudinally outwardly in the direction of the arrow (F) shown in FIG. 2E. When the actuator 104 is pulled, the elongate member 118 (and respective one or more gripping features 120c) simultaneously grip and pull on one segment 10a or 10b of the capsule 10 as the other segment 10b or 10a remains held in place between gripping features 120a, 120b (located in the inner cavity 110 and on the inner wall or surface 105 of the cover 106). This action causes the capsule 10 to separate (i.e., open) in the inner cavity 110 of the inhaler 100. At this time, some of the contents of the capsule 10 may exit the capsule 10 and enter the inner cavity 110. In some embodiments, prior to placing their mouth about the mouth section 112 of the inhaler 100, the user may first pull the actuator 104 and verify that the capsule 10 has been opened by looking through the visually transmissive section 106a of the cover 106. Once the user confirms the capsule 10 has been separated, the user may then lift the inhaler 100 to their mouth and inhale. As further discussed below, some of the dry powder contents such as pharmaceutical or nutraceutical may also remain in the separated segments 10a, 10b of the capsule 10. The user then inhales to receive the released capsule contents through the aperture 112a of the mouth section 112 (FIG. 2F). Airflow enters the inner cavity 110 via air intake ports 115 (FIG. 5A). As shown in FIG. 2G, after the user has inhaled the capsule contents (e.g., released pharmaceutical or nutraceutical), the actuator 104 can be pushed or automatically retract longitudinally inwardly in the direction of the arrow (F) back to the closed position and the cover 106 may be opened to remove the separated segments 10a, 10b of the empty capsule 10.

The air intake ports 115 can reside on the main body 102 adjacent the head 104a of the actuator 104 in the closed position. In this manner, the head 104a of the actuator 104 can provide a cap that protects the air intake port(s) 115 when the inhaler 100 is not in active use.

As discussed above, and shown in FIG. 3C, once the capsule 10 is separated, the two segments 10a, 10b cannot typically be reassembled, and therefore can occupy a longer space than the initial length $L_p$ of the intact capsule 10. The elongate member 118 can be spring-loaded (e.g., spring-loaded assembly 119) or otherwise biased to help to push the segments 10a, 10b of the empty capsule 10' out from the inner cavity 110 of the inhaler 100 when the cover 106 is opened, thereby allowing for easy removal of the segments 10a, 10b of the empty capsule 10' from the inhaler 100.

Referring now to FIGS. 4A-4C and FIGS. 5A-5D, example internal components of the capsule inhaler 100 are illustrated. Referring to FIGS. 4B and 4C, the main body 102 of the inhaler 100 can include a plurality of nozzles 130. The nozzles 130 are positioned and configured such that, when a user inhales, airflow (AF) enters the air intake port(s) 115 and is directed through the nozzles 130 into and/or within the inner cavity 110 of the inhaler 100 and into the separated segments 10a, 10b of the capsule 10 to efficiently and consistently deliver the dry powder pharmaceutical or nutraceutical to the user.

As shown in FIG. 4B, in some embodiments, the nozzles 130 may reside in the bottom portion 102b of the main body 102. The bottom portion 102b of the main body 102 may further include a backwall 111 that extends upwardly from an outer edge of the bottom portion 102b. The nozzles 130 extend laterally between the inner cavity 110 and the backwall 111 and opposite from the channel 113 which connects the aperture 112a of the mouth section 112 to the inner cavity 110. The nozzles 130 terminate adjacent to, but spaced part from, the backwall 111 leaving a gap (G) between the nozzles 130 and the backwall 111. When the top portion 102a of the main body 102 is secured with the bottom portion 102b, the nozzles 130 create air paths for air to flow from the intake port(s) 115 within the inhaler 100. In some embodiments, the air paths through the nozzles 130 may be tapered to narrow as they approach the inner cavity 110. As discussed further below, the gap (G) allows air to enter through the back end of the nozzles 130 and flow through the nozzles 130 into the inner cavity 110 (and into the separated segments 10a, 10b of the capsule 10) (see, e.g., FIGS. 5A-5D). In some embodiments, the backwall 111 may help to direct airflow (AF) from the intake port(s) 115 toward the back end of the nozzles 130.

In some embodiments, the inhaler 100 includes four nozzles 130₁, 130₂, 130₃, 130₄. As shown in FIGS. 5A-5D, the nozzles 130 are positioned such that airflow (AF) is directed to flowably entrain dry powder contents from the capsule 10, e.g., pharmaceutical or nutraceutical, which can remain within the separated segments 10a, 10b of the capsule 10, regardless of how the capsule 10 is oriented within the inner cavity 110 of the inhaler 10. FIG. 5A illustrates air flow (AF) within the inhaler 100 when a user inserts the capsule 10 with the longer segment of the capsule (i.e., segment 10b) adjacent to the right side (in the orientation shown) of the inner cavity 110 and the shorter segment of the capsule (i.e., segment 10a) adjacent to the left side (in the orientation shown) of the inner cavity 110 (relative to the orientation of the inhaler 100 shown in FIG. 5A). When the capsule 10 is oriented within the inhaler 100 as shown in FIG. 5A, nozzles $130_1$ and $130_3$ direct air into separated capsule segments 10a, 10b while nozzles $130_2$ and $130_4$ supply bypass air to entrain capsule contents released from the capsule segments 10a, 10b into the inner cavity 110. FIG. 5B illustrates air flow (AF) within the inhaler 100 when a user inserts the capsule 10 with the longer segment of the capsule (i.e., segment 10b) adjacent to the left side of the inner cavity 110 and the shorter segment of the capsule (i.e., segment 10a) adjacent to the right side of the inner cavity 110 (relative to the orientation of the inhaler 100 shown in FIG. 5B). When the capsule 10 is oriented within the inhaler 100 as shown in FIG. 5B, the nozzles 130 configured to flow into capsule segments 10a, 10b are nozzles $130_2$ and $130_4$ and nozzles $130_1$ and $130_3$ supply bypass air to the inner cavity 110.

As shown in FIGS. 5A-5B, in both orientations, when a user inhales, air flows (AF) through the intake port(s) 115 which can be formed in the main body 102 and is directed toward and through the nozzles 130. In some embodiments, two of the nozzles 130 may have a narrower airflow path or passageway (e.g., $130_1$ and $130_4$) over at least a major portion of their length than the other two nozzles (e.g., $130_2$ and $130_3$). In some embodiments, first and second pairs 130p of the nozzles 130 may be configured to direct air into the capsule segments 10a, 10b on only their corresponding side of the inner cavity 110 with little or no cross-flow or mixing between airflow provided by the two pairs of nozzles 130p until the exit channel 113 and/or mouth section 112.

As shown in FIG. 5D, in some embodiments, the inhaler 100 may include one or more additional intake ports 117 formed in the main body 102 and longitudinally spaced apart from intake port(s) 115. Similar to intake ports 115, intake ports 117 are configured to also direct air flow (AF) toward and through the nozzles 130. In some embodiments, the backwall 111 may also help to direct airflow (AF) from the intake port(s) 117 toward the back end of the nozzles 130. Including additional intake ports 117 longitudinally spaced apart from intake ports 115 may help to balance air flow (AF) through the nozzles 130 and within the inhaler 100. For example, air flow (AF) through intake ports 115 may primarily flow through one pair of nozzles 130p (i.e., $130_3$ and $130_4$) and air flow (AF) through intake ports 117 may primarily flow through the other pair of nozzles 130p (i.e., $130_1$ and $130_2$).

As shown in FIG. 5C, in some embodiments, nozzle exits 131 of the nozzles $130_1$, $130_2$ that reside at a location where airflow exits the corresponding nozzles 130 and enters into the inner cavity 110 may be slightly angled outwardly toward one end of the main body 102 of the inhaler 100 (the end further away from the actuator 104), while nozzle exits 132 of nozzles $130_3$, $130_4$ at a location where airflow exits the corresponding nozzles 130 and enters into the inner cavity 110 may be slightly angled outwardly toward the other end of the main body 102 of the inhaler 100 (the end closer to the actuator 104). The nozzle exits 131, 132 can angle away from an (imaginary) center line (CL) toward the end 10e of respective capsule segments 10a, 10b in the inner cavity 110. Thus, airflow (AF) entrains the dry powder and carries it to the aperture 112a of the mouth section 112 such that one pair of nozzles 130p (e.g., $130_1$ and $130_2$) entrain contents of one of the capsule segments 10a, 10b on the left side of the inner cavity 110 and the other pair of nozzles 130p (e.g., $130_3$ and $130_4$) entrain contents of the other capsule segment 10a, 10b on the right side of the inner cavity 110 (relative to the orientation of the inhaler 100 as shown in FIGS. 5A-5C). In other words, in some embodiments, airflow (AF) from each pair of nozzles 130p (i.e., $130_1$, $130_2$ and $130_3$, $130_4$) is directed such that it does not cross the center line (CL).

The inhaler 100 is configured to separate the capsule 10 such that adjacent ends of the separated segments 10a, 10b are spaced apart a distance $D_s$ between about 0.60 inches and about 1 inch. For example, in some embodiments, adjacent ends of the segments 10a, 10b are spaced apart a distance $D_s$ of about 0.67 inches. In other embodiments, adjacent ends of the segments 10a, 10b are spaced apart a distance $D_s$ of about 0.92 inches. The distance $D_s$ between adjacent ends of the separated segments 10a, 10b may have an effect on the allowable inlet air flow angle of attack into the open capsule segments 10a, 10b and powder dispersion capability of the inhaler 100. The distance $D_s$ is a function of the capsule size, inlet channel layout and the ability of the inhaler to accept capsule placement in both orientations.

In some embodiments, the shape and size of the inner cavity 110 of the inhaler 100 is designed to substantially match (within 10%-15%) of the volume of the capsule 10 and is configured to minimize volume and focus maximum flow velocity and energy into the separated capsule segments 10a, 10b. The focused airflow (AF) from the nozzles 130 can be constrained within a relatively small volume which may allow the inhaler 100 to provide efficient and consistent dry powder output, e.g., pharmaceutical or nutraceutical (e.g., dry powder) dispersion, emittance and deaggregation and which may also provide a high fine particle fraction.

The inhaler 100 can be tunable to provide low or high flow resistance of the airflow (AF) via the nozzles 130 and inner cavity 110 to facilitate different uses, different treatments, different size capsules and different formulations of capsule content.

FIG. 6 illustrates an end cross-section view of airflow (AF) within the inhaler 100 and airflow (AF) about and in the capsule 10. As shown in FIG. 6, air can be directed to circulate within the capsule segments 10a, 10b while held in the inhaler 100 to "scour" the inner surfaces of the separated capsule segments 10a, 10b. The air flow stream may be partially rotational but may also swirl into the separated capsule segments 10a, 10b to disperse and aerosolize the dry power agent released from the capsule 10. The tapered nozzles 130 with restricted inlet channel openings 131, 132, in addition to the closed cover 106 (and internal wall or surface 105), can cooperate to define a critical air flow resistance level of the inhaler 100. One or more of the nozzles 130 can be configured to provide an increase in air velocity as the airflow (AF) enters the capsule segments 10a, 10b to increase and/or maximize dry powder) dispersion during inhalation by the user. Where the inlet channel openings 131, 132 enter the inner cavity 110 may define the critical airflow choke point, the primary driver for inhaler airflow resistance level and air flow jet velocity entering the inner cavity 110 to do the work of powder dispersion and deaggregation. Tapered inlet channels 131, 132 enter the inner cavity 110 at locations of reduced cross-sectional area creating a nozzle effect and resulting in increased air flow velocity, jetting, and directional control of jets for efficient powder dispersion and deaggregation. Deaggregation occurs as powder in the capsule 10 is dispersed by the incoming air jets and agglomerates impact each other and capsule 10 or inner cavity 110 walls prior to exiting the mouth section 112. As used herein, the term "powder" may include (1) jet milled active pharmaceutical ingredient (API) (small particles typically having a mean particle size of about 2.5 microns) blended with milled excipients (larger particles typically having a mean particle size of about 60 microns), such as lactose and magnesium stearate; and (2) spray-dried powder which may contain API plus excipients. For spray-dried powder, the process normally produces particles in a low particle size range, e.g., all particles having a mean particle size of about 2.5 microns. Different powders will have different particle-particle attraction, powder-surface attraction, aggregation challenges and flow characteristics within the inhaler 100. Additional areas of powder impact and deaggregation may be the incorporation of an outlet grid or series of walls or obstructions 121 integrated between the inner cavity 110 and aperture 112*a* of the mouth section 112 (i.e., within channel 113) (see, e.g., FIG. 5D). See also, e.g., U.S. Pat. No. 9,027,551 to King et al., the disclosure of which is hereby incorporated herein in its entirety.

FIGS. 7A-7B further illustrate example gripping features 120*a*, 120*b*, 120*c* of the inhaler 100 according to embodiments of the present invention. As described herein, as the cover 106 is closed, the one or more gripping feature 120*a* of the inner surface or wall 105 contacts the first and same capsule segment 10*a* or 10*b* of the capsule 10 (depending on orientation within the inner cavity 110) as the one or more gripping feature 120*b* of the inner cavity 110, thereby securing the first segment 10*a*, 10*b* of the capsule 10 between the gripping features 120*a*, 120*b*. When the actuator 104 of the inhaler 100 is pulled longitudinally outwardly, the elongate member 118 (and respective one or more gripping feature 120*c*) simultaneously grips and pulls on another segment, the second segment 10*b* of the capsule 10 as the first segment 10*a* remains held in place between gripping features 120*a*, 120*b*. This action causes the capsule 10 to separate (i.e., open) in the inner cavity 110 of the inhaler 100.

FIGS. 8A-8R illustrate exemplary shapes and sizes of the gripping features 120. In some embodiments, one or more of the gripping features 120 can comprise teeth 120*t* within the inhaler 100 may be a rounded cylinder having a deep (FIG. 8A), medium (FIG. 8B) or shallow (FIG. 8C) profile. In some embodiments, one or more of the teeth 120*t* within the inhaler 100 may be an angled cylinder having a deep (FIG. 8D), medium (FIG. 8E) or shallow (FIG. 8F) profile. In some embodiments, one or more of the teeth 120*t* within the inhaler 100 may be convex in shape having a deep (FIG. 8G), medium (FIG. 8H) or shallow (FIG. 8I) profile. In some embodiments, one or more of the teeth 120*t* within the inhaler 100 may be concave in shape having a deep (FIG. 8J), medium (FIG. 8K) or shallow (FIG. 8L) profile. In some embodiments, one or more teeth 120*t* within the inhaler 100 may have a sharp or pointed edge with a deep (FIG. 8M), medium (FIG. 8N) or shallow (FIG. 8O) profile. In some embodiments, one or more the teeth 120*t* within the inhaler 100 may comprise opposing segments with a deep (FIG. 8P), medium (FIG. 8Q) or shallow (FIG. 8R) profile. For each of the tooth geometries described herein, the teeth 120*t* may be configured to engage or grip the capsule 10 without puncturing the capsule 10. Other gripping features can be used including knurled surfaces, for example.

In some embodiments, the capsule inhaler 100 may include a writable NFC tag and/or RFID label (not shown) secured to the main body 102. The NFC tag and/or RFID label may be used to store information such as time, date, and usage each time the inhaler 100 is used. This stored information may then be periodically synched by a patient (e.g., to a smart phone or computer) and/or communicated to the patient, doctor, pharmacy, etc., if needed.

The capsule inhaler 100 can be configured for receiving a size 0 capsule or size 3 capsule. The capsule size plays a role in powder capacity (i.e., dose amount), ease of handling (i.e., larger size 0 capsule may be easier to handle than the smaller size 3 capsule), ease of manufacturing (e.g., filling the capsule), and ease of marking (e.g., for counterfeiting).

The capsules 10 can be provided with various dry powder formulations with different active ingredients and different carrier and excipient ingredients. For example, the capsules 10 may be provided with ciclesonide, Advair® (fluticasone and salmeterol) or generics thereof, or other steroids, budesonide, azithromycin, tiotropium, Symbicort® or generics thereof, remdesivir, oxytocin, levodopa, dry pharmaceutical powders produced by spray-drying or other dry pharmaceutical powders, and vitamins such as Vitamin D and Zinc. In some embodiments, the dry power formulations may be blended with lactose as a carrier. In some embodiments, the capsule 10 may be provided with asthma or prevention of bronchospasm rescue medications, such as short acting beta agonists (SABA) (e.g., albuterol), long acting beta agonists (LABA) (e.g., salmeterol), corticosteroids such as fluticasone, fluticasone furoate, vilanterol, umeclidinium bromide, budesonide, mometesone, and double and triple combinations of known asthma and COPD drugs (e.g., Advair®, Symbicort®, Breo, Anoro, Trelegy). In some embodiments, the capsule 10 may be provided with COPD and prevention of bronchospasm medications, such as tiotropium, ipratropium, long-acting muscarinic antagonists (LAMA). In some embodiments, the capsule 10 may be provided with anti-infectives, antibiotics (e.g., tobramycin), antivirals, or anti-fungals. In some embodiments, the capsule 10 may be provided with cystic fibrosis medications such as mucalytics (mucus thinners). In some embodiments, the capsule 10 may be provided with medications to help pain, nervous system, or psychological therapy such as cannabinoids (i.e., CBD related drug compounds), fentanyl, or psilocybin. In some embodiments, the capsule 10 may be provided with excipients, bulking agents and/or carriers to reduce powder cohesiveness such as lactose, magnesium stearate, mannitol, or spray-dried excipients such as luceine. The capsule 10 may be provided with other known medications, excipients, bulking agents, and/or carriers. The inhaler 100 of the present invention may be used to deliver a variety of other known pharmaceuticals or nutraceuticals available in dry powder form.

The inhaler 100 of the present invention may be used for a variety of different treatments. In some embodiments, the inhaler 100 of the present invention may be used to deliver a pharmaceutical (e.g., a spray dried pharmaceutical powder) directly into the throat and/or esophagus of a subject to treat eosinophilic esophagitis (EoE). In some embodiments, the pharmaceutical is ciclesonide, budesinide, or a combination of fluticasone and salmeterol. The particle size of the pharmaceutical may be large enough such that a majority of the particles may not enter the subject's lungs (e.g., about 25 microns), and instead contact the throat and/or esophagus directly to treat inflammation or other problems with the esophagus. In some embodiments, the inhaler 100 of the present invention may be used to deliver a triple drug (pharmaceutical) therapy (i.e., three different pharmaceutical powders into a capsule 10). For example, in some embodiments, the pharmaceuticals of the triple drug therapy may include vilanterol, fluticasone furoate, umeclidinium bromide, or a combination thereof.

Large particles with relatively large mass will typically have more momentum while flowing and may fail to transition efficiently through the throat-bend of a subject resulting in drug deposition in the throat and/or esophagus. In some instances, the power pharmaceutical may stay on the surface of the throat and/or esophagus for a longer time period compared to, for example, swallowing a liquid pharmaceutical. In some embodiments, jet milling or spray drying relatively large particles may be utilized to generate the dry power agent (i.e., API) and/or carrier particles designed with relatively large size and mass to target the throat and/or esophagus. In some embodiments, a high percentage of the smaller particles may be removed by a sieving, which may result in a majority of the API reaching the throat and/or esophagus of the subject with fewer small carrier and/or API particles reaching the lungs of the subject. In some instances, carrier particles and/or API particles may be sieved to remove the finer particles (e.g., particles having a size less than 5 or 10 microns) prior to blending and filling of the capsule 10 or prior to directly filling into capsules 10 without blending.

In some embodiments, the d10 particle size distribution (i.e., 10% of the particles are X microns or less) may be about 30 microns. In some embodiments, the d50 particle size distribution (i.e., 50% of the particles are X microns or less) may be about 60 microns. In some embodiments, the d90 particle size distribution (i.e., 90% of the particles are X microns or less) may be about 100 microns. In some embodiments, the d10 particle size distribution may be in the range of about 35 microns to about 65 microns (e.g., the particle size distribution may be about 35, 40, 45, 50, 55, 60, or 65 microns). In some embodiments, the d50 particle size distribution may be in the range of about 95 microns to about 125 microns (e.g., the particle size distribution may be about 95, 100, 105, 110, 115, 120, or 125 microns). In some embodiments, the d90 particle size distribution may be in the range of about 160 microns to about 190 microns (e.g., the particle size distribution may be about 160, 165, 170, 175, 180, 185, or 190 microns).

In some embodiments, the inhaler 100 of the present invention may be used to deliver a pharmaceutical to a subject to treat a disease, such as asthma, chronic obstructive pulmonary disease (COPD), lung cancer and SARS-CoV-2 (COVID-19).

In some embodiments, the inhaler 100 of the present invention may be used to deliver a pharmaceutical to a subject to provide a hormone treatment via the stomach or lungs of the subject.

In some embodiments, the inhaler 100 of the present invention may be used to deliver a pharmaceutical (e.g., an antibiotic) to a subject to treat an infection in the subject's lungs.

In some embodiments, the inhaler 100 of the present invention may be used to deliver a nutraceutical to a subject to help promote health. For example, in some embodiments, the inhaler 100 may be used to inhale vitamins that may be deposited directly into a subject's stomach or lungs instead of swallowing them via a capsule 10. In addition, for subjects who may have difficulty swallowing larger capsules 10, in some embodiments, the inhaler 100 may be used to inhale nutraceuticals instead of swallowing the larger capsule 10.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

TABLE 1

| Exemplary Capsule Sizes and Corresponding Dimensions | | | | | | | | |
|---|---|---|---|---|---|---|---|---|
| CAPSULE SIZE | 000 | 00 | 0 | 1 | 2 | 3 | 4 | 5 |
| CAPACITY | | | | | | | | |
| Body Volume (ml) | 1.37 | 0.95 | 0.68 | 0.5 | 0.37 | 0.3 | 0.21 | 0.10 |
| Capsule capacity (mg) for powder density | | | | | | | | |
| 0.6 g/cc | 822 | 570 | 408 | 300 | 222 | 180 | 126 | 60 |
| 0.8 g/cc | 1096 | 760 | 544 | 400 | 296 | 240 | 168 | 80 |
| 1.0 g/cc | 1370 | 950 | 680 | 500 | 370 | 300 | 210 | 100 |
| 1.2 g/cc | 1644 | 1140 | 816 | 600 | 444 | 360 | 252 | 120 |
| WEIGHT | | | | | | | | |
| Average weight in mg | 163 | 127 | 102 | 78 | 65 | 50 | 39 | 28 |
| Tolerance in % | ±10 | ±10 | ±10 | ±10 | ±10 | ±10 | ±10 | ±10 |
| LENGTH | | | | | | | | |
| Cap Nominal (mm) | 13 | 11.8 | 10.7 | 9.8 | 9 | 8.1 | 7.2 | 6.2 |
| Tolerance (mm)* | ±0.4 | ±0.4 | ±0.4 | ±0.4 | ±0.4 | ±0.4 | ±0.4 | ±0.4 |
| Body Nominal (mm) | 22.2 | 20.2 | 18.5 | 16.6 | 15.2 | 13.6 | 12.2 | 9.3 |
| Tolerance (mm)* | ±0.4 | ±0.4 | ±0.4 | ±0.4 | ±0.4 | ±0.4 | ±0.4 | ±0.4 |
| OVERALL CLOSED LENGTH | | | | | | | | |
| Nominal Joined length (mm) | 25.9 | 23.5 | 21.4 | 19.3 | 17.8 | 15.8 | 14.4 | 11.4 |
| Tolerance (mm)* | ±0.4 | ±0.4 | ±0.4 | ±0.4 | ±0.4 | ±0.4 | ±0.4 | ±0.4 |
| NORMAL OUTSIDE DIAMETER | | | | | | | | |
| Cap Nominal (mm) | 9.96 | 8.55 | 7.66 | 6.93 | 6.37 | 5.85 | 5.33 | 4.91 |
| Tolerance (mm)* | ±0.06 | ±0.06 | ±0.06 | ±0.06 | ±0.06 | ±0.06 | ±0.06 | ±0.06 |
| Body Nominal (mm) | 9.61 | 8.2 | 7.32 | 6.61 | 6.07 | 5.57 | 5.06 | 4.65 |
| Tolerance (mm)* | ±0.06 | ±0.06 | ±0.06 | ±0.06 | ±0.06 | ±0.06 | ±0.06 | ±0.06 |

What is claimed is:

1. A capsule inhaler, comprising:

a main body comprising an inner cavity, a backwall, and at least one air intake port, wherein the inner cavity is sized and configured to receive a capsule containing a dry powder formulation;

a mouth section coupled to or integral with the main body and in fluid communication with the inner cavity;

an actuator coupled to the main body, the actuator comprising an elongate member attachable to an end portion of the capsule, wherein the actuator is configured to move between first and second positions to separate the capsule within the inner cavity;

at least four longitudinally spaced apart nozzles residing within the main body and in fluid communication with the inner cavity, wherein each of the nozzles extends between the inner cavity and backwall of the main body and opposite the mouth section terminating adjacent to, but spaced apart from, the backwall leaving a gap between the nozzles and the backwall; and a cover coupled to the main body, wherein one or more of the inner cavity, elongate member, and cover each are configured to engage with the capsule when inserted into the inner cavity and assist in separating the capsule to release the dry powder formulation into the inner cavity of the inhaler for inhalation by a subject, and wherein at least two of the nozzles are positioned and configured to direct airflow received from the at least one air intake port into separated segments of the capsule and at least another two of the nozzles are positioned and configured to direct bypass airflow received from the at least one air intake port into the inner cavity.

2. The capsule inhaler of claim 1, wherein the at least four longitudinally space apart nozzles consists of four nozzles.

3. The capsule inhaler of claim 1, wherein the longitudinally spaced apart nozzles comprises a first pair of nozzles and second pair of nozzles, wherein a first nozzle of the first pair of nozzles is configured to direct airflow only into a first capsule segment and a first nozzle of a second pair of nozzles is configured to direct airflow only into a second capsule segment, wherein the second nozzle of the first pair of nozzles is configured to direct airflow across the inner cavity over a first sub-length of the inner cavity and the second nozzle of the second pair of nozzles is configured to direct airflow across the inner cavity over a second sub-length of the inner cavity whereby airflow exiting from the second nozzle of the first pair of nozzles does not cross airflow exiting from the second nozzle of the second pair of nozzles.

4. The capsule inhaler of claim 3, wherein airflow exiting from each pair of nozzles is configured to be directed such that it does not cross an imaginary center line extending laterally across the inner cavity and between the first and second pairs of nozzles.

5. The capsule inhaler of claim 1, wherein two of the nozzles have a narrower airpath passageway than another two nozzles.

6. The capsule inhaler of claim 1, wherein airpath passageways of the nozzles are tapered to narrow at an exit end of the nozzles.

7. The capsule inhaler of claim 1, wherein at least two of the nozzles are configured to create a partially rotational airflow within the separated segments of the capsule.

8. The capsule inhaler of claim 1, wherein the elongate member of the actuator comprises a spring-loaded assembly that is configured to bias the actuator against the capsule when the capsule has been inserted into the inner cavity.

9. The capsule inhaler of claim 1, wherein the actuator further comprises a head portion coupled to the elongate member providing a location for a user to grip the actuator.

10. The capsule inhaler of claim 1, wherein the cover comprises a visually transmissive segment for allowing a user to see into the inner cavity of the inhaler when the cover is in a closed position.

11. The capsule inhaler of claim 1, further comprising the capsule, wherein the dry powder formulation within the capsule comprises a pharmaceutical or nutraceutical.

12. The capsule inhaler of claim 1, wherein the inner cavity is sized to hold a size 0 capsule.

13. The capsule inhaler of claim 1, wherein the inner cavity has a length between about 0.85 inch and about 1.25 inches.

14. The capsule inhaler of claim 1, wherein the actuator is configured to separate the capsule within the inner cavity such that adjacent ends of the separated segments of the capsule are spaced apart a distance between about 0.60 inches and about 1 inch.

15. A capsule inhaler, comprising:

a main body having an inner cavity formed therein, wherein the inner cavity is sized and configured to receive a capsule containing a dry powder formulation;

a mouth section coupled to or integral with the main body and in fluid communication with the inner cavity;

an actuator coupled to the main body, the actuator comprising an elongate member attachable to an end portion of the capsule, wherein the actuator is configured to move between first and second positions to separate the capsule within the inner cavity;

a first pair of nozzles and a second pair of nozzles, each pair of nozzles residing longitudinally spaced apart within the main body and in fluid communication with the inner cavity, wherein the first and second pair of nozzles extend between the inner cavity and a backwall of the main body and opposite the mouth section terminating adjacent to, but spaced apart from, the backwall leaving a gap between the pairs of nozzles and the backwall; and a cover coupled to the main body, wherein one or more of the inner cavity, elongate member, and cover each are configured to engage with the capsule when inserted into the inner cavity and assist in separating the capsule to release the dry powder formulation into the inner cavity of the inhaler for inhalation by a subject, and wherein one of each of the pairs of nozzles is sized and configured to direct airflow into a capsule segment, wherein the other of each of the pairs of nozzles is sized and configured to direct bypass air into and/or across the inner cavity.

16. The capsule inhaler of claim 15, wherein a first nozzle of the first pair of nozzles is configured to direct airflow only into a first capsule segment and a first nozzle of the second pair of nozzles is configured to direct airflow only into a second capsule segment, wherein the second nozzle of the first pair of nozzles is configured to directs airflow across the inner cavity over a first sub-length of the inner cavity and the second nozzle of the second pair of nozzles is configured to direct airflow across the inner cavity over a second sub-length of the inner cavity whereby airflow exiting from the second nozzle of the first pair of nozzles does not cross airflow exiting from the second nozzle of the second pair of nozzles.

17. The capsule inhaler of claim 15, wherein airflow exiting from each pair of nozzles is configured to be directed such that it does not cross an imaginary centerline extending laterally across the inner cavity and between the two pairs of nozzles.

18. The capsule inhaler of claim 15, wherein two of the nozzles have a narrower airpath passageway than the other two nozzles.

19. The capsule inhaler of claim 15, wherein airway paths of the nozzles are tapered to narrow at an exit end of the nozzles.

20. The capsule inhaler of claim 15, wherein the pairs of nozzles are configured to creates a partially rotational airflow within separated segments of the capsule.

21. The capsule inhaler of claim 15, wherein the elongate member of the actuator comprises a spring-loaded assembly that is configured to bias the elongate member against the capsule when the capsule has been inserted into the inner cavity.

22. The capsule inhaler of claim 15, wherein the actuator further comprises a head portion coupled to the elongate member providing a location for a user to grip the actuator.

23. The capsule inhaler of claim 15, wherein the cover comprises a visually transmissive segment for allowing a user to see into the inner cavity of the inhaler when the cover is in a closed position.

24. The capsule inhaler of claim 15, further comprising the capsule, wherein the pharmaceutical or nutraceutical contained within the capsule is in a dry powder form.

25. The capsule inhaler of claim 15, wherein the inner cavity is sized and configured to receive a capsule having a length between about 0.5 inches and 1 inch.

26. The capsule inhaler of claim 15, wherein the inner cavity has a length between about 0.85 inch and about 1.25 inches.

27. The capsule inhaler of claim 15, wherein the inner cavity is sized to hold a size 0 capsule.

28. The capsule inhaler of claim 15, wherein the actuator is configured to separate the capsule within the inner cavity such that adjacent ends of separated segments of the capsule are spaced apart a distance between about 0.60 inches and about 1 inch.

\* \* \* \* \*